(12) United States Patent
Johns et al.

(10) Patent No.: US 9,482,684 B2
(45) Date of Patent: Nov. 1, 2016

(54) CENTRIFUGE SYSTEM AND WORKFLOW

(71) Applicant: Beckman Coulter, Inc., Brea, CA (US)

(72) Inventors: Charles W. Johns, Brownsburg, IN (US); Stephen Otts, Fishers, IN (US)

(73) Assignee: Beckman Coulter, Inc., Brea, CA (US)

( * ) Notice: Subject to any disclaimer, the term of this patent is extended or adjusted under 35 U.S.C. 154(b) by 842 days.

(21) Appl. No.: 13/671,361

(22) Filed: Nov. 7, 2012

(65) Prior Publication Data

US 2013/0123089 A1 May 16, 2013

Related U.S. Application Data

(60) Provisional application No. 61/556,667, filed on Nov. 7, 2011, provisional application No. 61/616,994, filed on Mar. 28, 2012, provisional application No. 61/680,066, filed on Aug. 6, 2012.

(51) Int. Cl.
*G01N 35/10* (2006.01)
*B65G 47/28* (2006.01)
(Continued)

(52) U.S. Cl.
CPC ......... *G01N 35/1009* (2013.01); *B01D 21/262* (2013.01); *B04B 7/02* (2013.01); *B04B 7/08* (2013.01); *B04B 9/146* (2013.01);
(Continued)

(58) Field of Classification Search
CPC ................... G01N 35/00732; G01N 35/0099; G01N 35/04; G01N 2035/00495; G01N 2035/0462; G01N 2035/1025; B04B 2011/046; B04B 2013/006
See application file for complete search history.

(56) References Cited

U.S. PATENT DOCUMENTS 3,158,765 A 11/1964 Prolgreen
4,052,161 A 10/1977 Atwood et al.
(Continued)

FOREIGN PATENT DOCUMENTS

CA 1 282 692 A1 4/1991
CN 1127887 A 7/1996
(Continued)

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA.
(Continued)

*Primary Examiner* — Timothy Cleveland
(74) *Attorney, Agent, or Firm* — Kilpatrick Townsend & Stockton LLP

(57) ABSTRACT

Systems, methods and apparatus are described for a centrifuge module of a laboratory analysis system. Specimen containers may be weighed, loaded into a centrifuge adapter, and transported to a centrifuge module by an adapter shuttle. A centrifuge adapter gripper may transport the centrifuge adapter into a centrifuge for centrifugation. The centrifuge adapter may be transported by the centrifuge adapter gripper to an adapter shuttle for unloading of the specimen containers, which may be performed by a specimen container gripper. A centrifuge drawer that allows a centrifuge to be extended from its installed position is also described. Additional embodiments pertain to a sequence for replacing, in a centrifuge, a set of centrifuge adapters that have been centrifuged with a set of centrifuge adapters that have not been centrifuged. A sequence for loading specimen containers into centrifuge adapters is also described.

12 Claims, 25 Drawing Sheets

(51) Int. Cl.

| | | |
|---|---|---|
| *B01D 21/26* | (2006.01) | |
| *B04B 7/08* | (2006.01) | |
| *B04B 15/00* | (2006.01) | |
| *B25J 11/00* | (2006.01) | |
| *B04B 9/14* | (2006.01) | |
| *G01N 35/00* | (2006.01) | |
| *G01N 35/04* | (2006.01) | |
| *G01B 11/02* | (2006.01) | |
| *G01B 11/08* | (2006.01) | |
| *G01B 11/10* | (2006.01) | |
| *G01M 1/14* | (2006.01) | |
| *G01N 21/27* | (2006.01) | |
| *B04B 7/02* | (2006.01) | |
| *B04B 13/00* | (2006.01) | |
| *B65D 51/24* | (2006.01) | |
| *G01L 19/08* | (2006.01) | |
| *B04B 11/04* | (2006.01) | |
| *B01L 3/00* | (2006.01) | |

(52) U.S. Cl.
CPC .............. *B04B 13/00* (2013.01); *B04B 15/00* (2013.01); *B25J 11/00* (2013.01); *B65D 51/24* (2013.01); *B65G 47/28* (2013.01); *G01B 11/02* (2013.01); *G01B 11/08* (2013.01); *G01B 11/10* (2013.01); *G01L 19/08* (2013.01); *G01M 1/14* (2013.01); *G01N 21/27* (2013.01); *G01N 35/0099* (2013.01); *G01N 35/00732* (2013.01); *G01N 35/04* (2013.01); *G01N 35/10* (2013.01); *B01L 3/5021* (2013.01); *B04B 2011/046* (2013.01); *B04B 2013/006* (2013.01); *G01N 2035/00495* (2013.01); *G01N 2035/0405* (2013.01); *G01N 2035/0462* (2013.01); *G01N 2035/0491* (2013.01); *G01N 2035/1025* (2013.01); *G01N 2035/1032* (2013.01); *Y10T 29/49826* (2015.01)

(56) References Cited

U.S. PATENT DOCUMENTS

| | | |
|---|---|---|
| 4,101,070 A | 7/1978 | Hoare et al. |
| 4,119,381 A | 10/1978 | Muka et al. |
| 4,250,266 A | 2/1981 | Wade |
| 4,401,189 A | 8/1983 | Majewski |
| 4,486,539 A | 12/1984 | Ranki et al. |
| 4,501,495 A | 2/1985 | Faulkner et al. |
| 4,530,056 A | 7/1985 | MacKinnon et al. |
| 4,593,238 A | 6/1986 | Yamamoto |
| 4,593,239 A | 6/1986 | Yamamoto |
| 4,673,657 A | 6/1987 | Christian |
| 4,674,640 A | 6/1987 | Asa et al. |
| 4,676,952 A | 6/1987 | Edelmann et al. |
| 4,683,195 A | 7/1987 | Mullis et al. |
| 4,683,202 A | 7/1987 | Mullis |
| 4,751,177 A | 6/1988 | Stabinsky |
| 4,780,817 A | 10/1988 | Lofgren |
| 4,800,159 A | 1/1989 | Mullis et al. |
| 4,851,330 A | 7/1989 | Kohne |
| 4,865,986 A | 9/1989 | Coy et al. |
| 4,943,415 A | 7/1990 | Przybylowicz et al. |
| 4,947,094 A | 8/1990 | Dyer et al. |
| 4,950,613 A | 8/1990 | Arnold, Jr. et al. |
| 5,055,393 A | 10/1991 | Kwoh et al. |
| 5,055,408 A | 10/1991 | Higo et al. |
| 5,075,853 A | 12/1991 | Luke, Jr. |
| 5,118,191 A | 6/1992 | Hopkins |
| 5,147,529 A | 9/1992 | Lee et al. |
| 5,154,888 A | 10/1992 | Zander et al. |
| 5,158,895 A | 10/1992 | Ashihara et al. |
| 5,168,766 A | 12/1992 | Stoffel |
| 5,179,329 A | 1/1993 | Nishikawa et al. |
| 5,185,439 A | 2/1993 | Arnold, Jr. et al. |
| 5,186,827 A | 2/1993 | Liberti et al. |
| 5,190,136 A | 3/1993 | Grecksch et al. |
| 5,196,168 A | 3/1993 | Muszak et al. |
| 5,205,393 A | 4/1993 | Malow et al. |
| 5,229,297 A | 7/1993 | Schnipelsky et al. |
| 5,234,665 A | 8/1993 | Ohta et al. |
| 5,244,055 A | 9/1993 | Shimizu |
| 5,283,174 A | 2/1994 | Arnold et al. |
| 5,283,739 A | 2/1994 | Summerville et al. |
| 5,288,463 A | 2/1994 | Chemelli |
| 5,330,916 A | 7/1994 | Williams et al. |
| 5,350,564 A | 9/1994 | Mazza et al. |
| 5,351,801 A | 10/1994 | Markin et al. |
| 5,362,291 A | 11/1994 | Williamson, IV |
| 5,366,896 A | 11/1994 | Margrey et al. |
| 5,374,395 A | 12/1994 | Robinson et al. |
| 5,375,898 A | 12/1994 | Ohmori et al. |
| 5,380,487 A | 1/1995 | Choperena et al. |
| 5,388,682 A | 2/1995 | Dudley |
| 5,389,339 A | 2/1995 | Petschek et al. |
| 5,397,709 A | 3/1995 | Berndt |
| 5,399,491 A | 3/1995 | Kacian et al. |
| 5,403,711 A | 4/1995 | Walder et al. |
| 5,415,839 A | 5/1995 | Zaun et al. |
| 5,422,271 A | 6/1995 | Chen et al. |
| 5,427,930 A | 6/1995 | Birkenmeyer et al. |
| 5,437,990 A | 8/1995 | Burg et al. |
| 5,443,791 A | 8/1995 | Cathcart et al. |
| 5,447,687 A | 9/1995 | Lewis et al. |
| 5,449,602 A | 9/1995 | Royer et al. |
| 5,462,881 A | 10/1995 | Perlman |
| 5,466,574 A | 11/1995 | Liberti et al. |
| 5,480,784 A | 1/1996 | Kacian et al. |
| 5,482,834 A | 1/1996 | Gillespie |
| 5,504,345 A | 4/1996 | Bartunek et al. |
| 5,514,550 A | 5/1996 | Findlay et al. |
| 5,525,300 A | 6/1996 | Danssaert et al. |
| 5,527,673 A | 6/1996 | Reinhartz et al. |
| 5,536,649 A | 7/1996 | Fraiser et al. |
| 5,538,849 A | 7/1996 | Uematsu et al. |
| 5,554,516 A | 9/1996 | Kacian et al. |
| 5,563,037 A | 10/1996 | Sutherland et al. |
| 5,578,270 A | 11/1996 | Reichler et al. |
| 5,582,796 A | 12/1996 | Carey et al. |
| 5,585,242 A | 12/1996 | Bouma et al. |
| 5,585,481 A | 12/1996 | Arnold, Jr. et al. |
| 5,587,128 A | 12/1996 | Wilding et al. |
| 5,589,333 A | 12/1996 | Bagasra et al. |
| 5,602,042 A | 2/1997 | Farber |
| 5,604,130 A | 2/1997 | Warner et al. |
| 5,612,200 A | 3/1997 | Dattagupta et al. |
| 5,612,525 A | 3/1997 | Apter et al. |
| 5,623,415 A | 4/1997 | O'Bryan et al. |
| 5,628,962 A | 5/1997 | Kanbara et al. |
| 5,637,275 A | 6/1997 | Carey et al. |
| 5,639,599 A | 6/1997 | Ryder et al. |
| 5,639,604 A | 6/1997 | Arnold et al. |
| 5,641,658 A | 6/1997 | Adams et al. |
| 5,652,489 A | 7/1997 | Kawakami |
| 5,653,940 A | 8/1997 | Carey et al. |
| 5,656,493 A | 8/1997 | Mullis et al. |
| 5,665,554 A | 9/1997 | Reeve et al. |
| 5,679,553 A | 10/1997 | Van Gemen et al. |
| 5,686,272 A | 11/1997 | Marshall et al. |
| 5,702,950 A | 12/1997 | Tajima |
| 5,705,062 A | 1/1998 | Knobel |
| 5,714,380 A | 2/1998 | Neri et al. |
| 5,720,923 A | 2/1998 | Haff et al. |
| 5,723,591 A | 3/1998 | Livak et al. |
| 5,730,938 A | 3/1998 | Carbonari et al. |
| 5,735,587 A | 4/1998 | Malin et al. |
| 5,741,708 A | 4/1998 | Carey et al. |
| 5,746,978 A | 5/1998 | Bienhaus et al. |
| 5,750,338 A | 5/1998 | Collins et al. |
| 5,773,268 A | 6/1998 | Korenberg et al. |
| 5,779,981 A | 7/1998 | Danssaert et al. |
| 5,786,182 A | 7/1998 | Catanzariti et al. |
| 5,795,547 A | 8/1998 | Moser et al. |

(56) References Cited

U.S. PATENT DOCUMENTS

| | | |
|---|---|---|
| 5,798,263 A | 8/1998 | Wood et al. |
| 5,814,008 A | 9/1998 | Chen et al. |
| 5,814,276 A | 9/1998 | Riggs |
| 5,814,961 A | 9/1998 | Imahashi |
| 5,827,653 A | 10/1998 | Sammes et al. |
| 5,846,489 A | 12/1998 | Bienhaus et al. |
| 5,846,491 A | 12/1998 | Choperena et al. |
| 5,846,726 A | 12/1998 | Nadeau et al. |
| 5,857,955 A | 1/1999 | Phillips et al. |
| 5,866,336 A | 2/1999 | Nazarenko et al. |
| 5,881,781 A | 3/1999 | Bishop |
| 5,882,903 A | 3/1999 | Andrevski et al. |
| 5,895,631 A | 4/1999 | Tajima et al. |
| 5,897,090 A | 4/1999 | Smith et al. |
| 5,897,783 A | 4/1999 | Howe et al. |
| 5,914,230 A | 6/1999 | Liu et al. |
| 5,919,622 A | 7/1999 | Macho et al. |
| 5,922,591 A | 7/1999 | Anderson et al. |
| 5,925,517 A | 7/1999 | Tyagi et al. |
| 5,928,907 A | 7/1999 | Woudenberg et al. |
| 5,948,673 A | 9/1999 | Cottingham |
| 5,966,309 A | 10/1999 | O'Bryan et al. |
| 5,994,056 A | 11/1999 | Higuchi |
| 6,011,508 A | 1/2000 | Perreault et al. |
| 6,033,574 A | 3/2000 | Siddiqi |
| 6,033,880 A | 3/2000 | Haff et al. |
| 6,043,880 A | 3/2000 | Andrews et al. |
| 6,049,745 A | 4/2000 | Douglas et al. |
| 6,056,106 A | 5/2000 | van Dyke, Jr. et al. |
| 6,060,022 A | 5/2000 | Pang et al. |
| 6,063,340 A | 5/2000 | Lewis et al. |
| 6,068,978 A | 5/2000 | Zaun et al. |
| 6,071,395 A | 6/2000 | Lange |
| 6,100,079 A | 8/2000 | Tajima |
| 6,110,676 A | 8/2000 | Coull et al. |
| 6,110,678 A | 8/2000 | Weisburg et al. |
| 6,117,398 A | 9/2000 | Bienhaus et al. |
| 6,129,428 A | 10/2000 | Helwig et al. |
| 6,150,097 A | 11/2000 | Tyagi et al. |
| 6,165,778 A | 12/2000 | Kedar |
| 6,171,780 B1 | 1/2001 | Pham et al. |
| 6,212,448 B1 | 4/2001 | Xydis |
| 6,277,332 B1 | 8/2001 | Sucholeiki |
| 6,300,068 B1 | 10/2001 | Burg et al. |
| 6,300,138 B1 | 10/2001 | Gleason et al. |
| 6,306,658 B1 | 10/2001 | Turner et al. |
| 6,333,008 B1 | 12/2001 | Leistner et al. |
| 6,335,166 B1 | 1/2002 | Ammann et al. |
| 6,353,774 B1 | 3/2002 | Goldenberg et al. |
| 6,368,872 B1 | 4/2002 | Juranas |
| 6,370,452 B1 | 4/2002 | Pfister |
| 6,374,989 B1 | 4/2002 | van Dyke, Jr. et al. |
| 6,377,888 B1 | 4/2002 | Olch |
| 6,429,016 B1 | 8/2002 | McNeil |
| 6,436,349 B1 | 8/2002 | Carey et al. |
| 6,444,171 B1 | 9/2002 | Sakazume et al. |
| RE37,891 E | 10/2002 | Collins et al. |
| 6,458,324 B1 | 10/2002 | Schinzel |
| 6,520,313 B1 | 2/2003 | Kaarakainen et al. |
| 6,548,026 B1 | 4/2003 | Dales et al. |
| 6,586,234 B1 | 7/2003 | Burg et al. |
| 6,586,255 B1 | 7/2003 | Hubert et al. |
| 6,597,450 B1 | 7/2003 | Andrews et al. |
| 6,599,476 B1 | 7/2003 | Watson et al. |
| 6,605,213 B1 | 8/2003 | Ammann et al. |
| 6,629,028 B2 | 9/2003 | Paromtchik et al. |
| 6,633,785 B1 | 10/2003 | Kasahara et al. |
| 6,692,708 B2 | 2/2004 | Chandler, Jr. |
| 6,764,649 B2 | 7/2004 | Ammann |
| 6,770,883 B2 | 8/2004 | Mc Neal et al. |
| 6,818,183 B2 | 11/2004 | Hajduk et al. |
| 6,890,742 B2 | 5/2005 | Ammann et al. |
| 6,919,058 B2 | 7/2005 | Andersson et al. |
| 6,919,175 B1 | 7/2005 | Bienhaus et al. |
| 6,941,200 B2 | 9/2005 | Sonoyama et al. |
| 6,993,176 B2 | 1/2006 | Yamagishi et al. |
| 6,999,847 B2 | 2/2006 | Barry et al. |
| 7,028,831 B2 | 4/2006 | Veiner |
| 7,033,820 B2 | 4/2006 | Ammann et al. |
| 7,045,358 B2 | 5/2006 | Chandler, Jr. |
| 7,071,006 B2 | 7/2006 | Tajima et al. |
| 7,078,698 B2 | 7/2006 | Itoh |
| 7,118,892 B2 | 10/2006 | Ammann et al. |
| 7,135,145 B2 | 11/2006 | Ammann et al. |
| 7,174,836 B2 | 2/2007 | Marino et al. |
| 7,264,111 B2 | 9/2007 | Veiner |
| 7,267,795 B2 | 9/2007 | Ammann et al. |
| 7,269,480 B2 | 9/2007 | Hashimoto et al. |
| 7,273,749 B1 | 9/2007 | Wittwer et al. |
| 7,288,229 B2 | 10/2007 | Turner et al. |
| 7,362,258 B2 | 4/2008 | Kawabe et al. |
| 7,419,830 B2 | 9/2008 | Canos et al. |
| 7,463,948 B2 | 12/2008 | Orita |
| 7,473,897 B2 | 1/2009 | Braendle et al. |
| 7,482,143 B2 | 1/2009 | Ammann et al. |
| 7,499,581 B2 | 3/2009 | Tribble et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,688,448 B2 | 3/2010 | Bamberg et al. |
| 7,771,659 B2 | 8/2010 | Ziegler |
| 8,074,578 B2 | 12/2011 | Thornton |
| 8,192,992 B2 | 6/2012 | Ammann et al. |
| 2002/0025064 A1 | 2/2002 | Itoh |
| 2002/0028489 A1 | 3/2002 | Ammann et al. |
| 2002/0031768 A1 | 3/2002 | McMillan et al. |
| 2002/0077239 A1 | 6/2002 | Evans, III et al. |
| 2002/0086417 A1 | 7/2002 | Chen |
| 2002/0098117 A1 | 7/2002 | Ammann et al. |
| 2002/0123156 A1 | 9/2002 | Tajima |
| 2002/0137194 A1 | 9/2002 | Ammann et al. |
| 2002/0137197 A1 | 9/2002 | Ammann et al. |
| 2002/0146347 A1 | 10/2002 | McNeil |
| 2002/0147515 A1 | 10/2002 | Fava et al. |
| 2003/0026736 A1 | 2/2003 | Hajduk et al. |
| 2003/0027206 A1 | 2/2003 | Ammann et al. |
| 2003/0054542 A1 | 3/2003 | Burns et al. |
| 2003/0129614 A1 | 7/2003 | Parameswaran et al. |
| 2003/0190755 A1 | 10/2003 | Turner et al. |
| 2003/0213313 A1 | 11/2003 | Katagi |
| 2003/0223916 A1 | 12/2003 | Testrut et al. |
| 2004/0029260 A1 | 2/2004 | Hansen et al. |
| 2004/0076983 A1 | 4/2004 | Karlsen |
| 2004/0087426 A1 | 5/2004 | Lattanzi |
| 2004/0115796 A1 | 6/2004 | Burns |
| 2004/0158355 A1 | 8/2004 | Holmqvist et al. |
| 2004/0184959 A1 | 9/2004 | Itoh |
| 2004/0206419 A1 | 10/2004 | Ganz et al. |
| 2004/0213651 A1 | 10/2004 | Malin |
| 2005/0130198 A1 | 6/2005 | Ammann et al. |
| 2005/0158212 A1 | 7/2005 | Yavilevich |
| 2005/0163354 A1 | 7/2005 | Ziegler |
| 2005/0207937 A1 | 9/2005 | Itoh |
| 2005/0220670 A1 | 10/2005 | Palmieri et al. |
| 2005/0233370 A1 | 10/2005 | Ammann et al. |
| 2005/0239127 A1 | 10/2005 | Ammann et al. |
| 2005/0266489 A1 | 12/2005 | Ammann et al. |
| 2005/0271555 A1 | 12/2005 | Itoh |
| 2006/0003373 A1 | 1/2006 | Ammann et al. |
| 2006/0014295 A1 | 1/2006 | Ziegler |
| 2006/0020370 A1 | 1/2006 | Abramson |
| 2006/0148063 A1 | 7/2006 | Fauzi et al. |
| 2006/0228268 A1 | 10/2006 | Heimberg et al. |
| 2007/0044676 A1 | 3/2007 | Clark et al. |
| 2007/0059209 A1 | 3/2007 | Pang et al. |
| 2007/0100498 A1 | 5/2007 | Matsumoto et al. |
| 2007/0110634 A1 | 5/2007 | Heimberg et al. |
| 2007/0134131 A1 | 6/2007 | Watson et al. |
| 2007/0179690 A1 | 8/2007 | Stewart |
| 2007/0184548 A1 | 8/2007 | Tan et al. |
| 2007/0193859 A1 | 8/2007 | Kyuyoku et al. |
| 2007/0196237 A1 | 8/2007 | Neuzil et al. |
| 2007/0208440 A1 | 9/2007 | Bliss et al. |
| 2007/0225901 A1 | 9/2007 | Yamaguchi |

(56) References Cited

U.S. PATENT DOCUMENTS

| | | |
|---|---|---|
| 2007/0225906 A1 | 9/2007 | Ikeda |
| 2008/0014181 A1 | 1/2008 | Ariff et al. |
| 2008/0015470 A1 | 1/2008 | Sarstedt |
| 2008/0056958 A1 | 3/2008 | Vijay et al. |
| 2008/0069730 A1 | 3/2008 | Itoh |
| 2008/0138249 A1 | 6/2008 | Itoh |
| 2008/0167817 A1 | 7/2008 | Hessler et al. |
| 2008/0241837 A1 | 10/2008 | Ammann et al. |
| 2008/0255683 A1 | 10/2008 | Takahashi et al. |
| 2008/0268528 A1 | 10/2008 | Ammann et al. |
| 2008/0274511 A1 | 11/2008 | Tan et al. |
| 2008/0297769 A1 | 12/2008 | Bamberg et al. |
| 2009/0029352 A1 | 1/2009 | Ammann et al. |
| 2009/0029871 A1 | 1/2009 | Ammann et al. |
| 2009/0029877 A1 | 1/2009 | Ammann et al. |
| 2009/0030551 A1 | 1/2009 | Hein et al. |
| 2009/0035185 A1 | 2/2009 | Tsujimura et al. |
| 2009/0042281 A1 | 2/2009 | Chang et al. |
| 2009/0047179 A1 | 2/2009 | Ping et al. |
| 2009/0117620 A1 | 5/2009 | Fritchie et al. |
| 2009/0318276 A1 | 12/2009 | Miler |
| 2009/0324032 A1 | 12/2009 | Chen |
| 2010/0018330 A1 | 1/2010 | Marty et al. |
| 2010/0115887 A1 | 5/2010 | Schroeder et al. |
| 2010/0129789 A1 | 5/2010 | Self et al. |
| 2010/0141756 A1 | 6/2010 | Grote et al. |
| 2010/0261595 A1 | 10/2010 | Schaefer et al. |
| 2010/0291619 A1 | 11/2010 | Robinson et al. |
| 2011/0065193 A1 | 3/2011 | Kitagawa et al. |
| 2011/0226584 A1 | 9/2011 | Ek |
| 2012/0129673 A1 | 5/2012 | Fukugaki et al. |
| 2013/0125675 A1 | 5/2013 | Mueller et al. |
| 2013/0126302 A1 | 5/2013 | Johns et al. |
| 2013/0128035 A1 | 5/2013 | Johns et al. |
| 2013/0129166 A1 | 5/2013 | Mueller et al. |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1974781 A | 6/2007 |
| CN | 102023227 A | 4/2011 |
| DE | 35 10 797 C2 | 1/1988 |
| DE | 696 33 532 T2 | 2/2006 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 819 941 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 764 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |
| JP | 01-211500 A1 | 8/1989 |
| JP | 02-025754 A2 | 1/1990 |
| JP | 05-184397 A | 7/1993 |
| JP | 09-329602 A | 7/1993 |
| JP | 05-219933 A | 8/1993 |
| JP | 05-281239 A | 10/1993 |
| JP | 06-011512 A | 1/1994 |
| JP | 06-197797 A | 7/1994 |
| JP | 06-327476 A | 11/1994 |
| JP | 07-75544 A | 3/1995 |
| JP | 07-191042 A | 7/1995 |
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 10-062426 A | 3/1998 |
| JP | 11-503315 A | 3/1999 |
| JP | 2000-500331 A | 1/2000 |
| JP | 3007571 B2 | 2/2000 |
| JP | 2001-503730 A | 3/2001 |
| JP | 2002-296286 A | 10/2002 |
| JP | 2006-317330 A | 11/2006 |
| JP | 2007-249632 A | 9/2007 |
| JP | 2008-032652 A2 | 2/2008 |
| JP | 4511034 A | 5/2010 |
| JP | 4662580 A | 3/2011 |
| WO | 88/01302 A1 | 2/1988 |
| WO | 88/10315 A1 | 12/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/29602 A1 | 9/1996 |
| WO | 96/31781 A1 | 10/1996 |
| WO | 96/40990 A1 | 12/1996 |
| WO | 97/03348 A1 | 1/1997 |

(56) References Cited

FOREIGN PATENT DOCUMENTS

| WO | 97/05492 A1 | 2/1997 |
|---|---|---|
| WO | 97/16561 A1 | 5/1997 |
| WO | 97/31105 A1 | 8/1997 |
| WO | 97/34908 A1 | 9/1997 |
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 00/08472 A2 | 2/2000 |
| WO | 00/08472 A3 | 2/2000 |
| WO | 00/15481 A1 | 3/2000 |
| WO | 00/38046 A1 | 6/2000 |
| WO | 00/67547 A2 | 11/2000 |
| WO | 01/44510 A2 | 6/2001 |
| WO | 03/046412 A1 | 6/2003 |
| WO | 03/097808 A2 | 11/2003 |
| WO | 2004/013640 A1 | 2/2004 |
| WO | 2006/021052 A1 | 3/2006 |
| WO | 2006/068470 A1 | 3/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2009/068555 A1 | 6/2009 |
| WO | 2009/097263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2011/013701 A1 | 2/2011 |
| WO | 2011/028166 A1 | 3/2011 |
| WO | 2012/090795 A1 | 7/2012 |
| WO | 2012/158541 A1 | 11/2012 |

OTHER PUBLICATIONS

ABI PRISM® 373 DNA Sequencer With XL Upgrade—User's Manual, Mar. 2001, TOC-iii—TOC-v & 6-11-6-16, Applied Biosystems, USA.

Abravaya, "Strategies to Avoid Amplicon Contamination," in Nucleic Acid.Amplification Technologies: Application to Disease Diagnosis, 1997, pp. 125-133, Eaton Pub. Co., Natick, USA.

Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA.

Akduman et al., "Evaluation of a Strand Displacement Amplification Assay (BD ProbeTec-SDA) for Detection of Neisseria gonorrhoeae in Urine Specimens," J.Clin. Microbiol., 2002, 40(1):281-282, American Society for Microbiology, Washington D.C., USA.

Amplification Technical Bulletin, "Comparison of TMA with PCR and LCR Amplification Methods," undated, Gen-Probe Incorporated, San Diego, USA, 1 page.

Analog Device; "±5 $g$ to ±5 $g$, Low Noise, Low Power, Single/Dual Axis / MEMS.® Accelerometers,"; http://hibp.ecse.rpi.edu/~connor.education/EISpecs/ADXL150_250_0.pdf; Jan. 1, 1998; pp. 1-15.

Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.

Armstrong et al., 1996, "Automated high throughput RT-PCR," Laboratory Robotics and Automation 8:311-315, VCH Publishers, USA.

Astle, "Standards in Robotics and Instrucmentation," Society Updates, Working Group Updates, and Conference Highlights, J. Biomol. Screen., 1996, 1(4):161-172, Sage Publications, USA.

Bailey et al., "Robotic Nucleic Acid Isolation Using a Magnetic Bead Resin and an Automated Liquid Handler for Biological Agent Simulants,", JALA, Dec. 2003, 8:113-120.

Bassam. "Nucleic Acid Sequence Detection Systems: Revolutionary Automation for Monitoring and Reporting PCR Products" Australasian Biotechnology, 1996, 6:285-294, Australian Biotechnology Association, Australia.

Belgrader et al., "Automated DNA Purification and Amplification from Blood-Stained Cards Using a Robotic Workstation," Short Technical Reports, Biotechniques, 1995, 19(9):426-432, Informa Healthcare USA, Inc., UK.

Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.

Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.

Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.

Boyd et al., "Robotics and the changing face of the clinical laboratory," Clin. Chem., 1996, 42(12):1901-1910, Washington DC American Association for Clinical Chemistry, USA.

Brochure, "Amplified Mycobacteria Direct Tests," undated, Gen-Probe Incorporated, San Diego, USA, 6 pages.

Brochure, "Introducing the Amplified Mycobacterium Tuberculosis Direct (MTD) Test from Gen-Probe," Oct. 1996, Gen-Probe Incorporated, San Diego, USA, 2 pages.

Brochure, "The Future of Amplification Technology has Arrived," Oct. 1995, Gen-Probe Incorporated, San Diego, USA, 4 pages.

Buhlmann et al., "An Open Software Environment to Optimize the Productivity of Robotized Laboratories," J. Chromatogra. Sci., 1994, 32:243-248, Preston Technical Abstracts, Niles, USA.

Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA.

Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.

Caprari, G. et al.; "The autonomous Micro Robot "Alice": a platform for scientific and commercial applications"; Proceedings of the 1998 International Symposium on Micromechatronics and Human Science, Nagoya, Japan; Nov. 25-28, 1998; pp. 1-5.

Carlson et al., "Laboratory Detection of Chlamydia trachomatis, Neisseria gonorrhoeae, and Other Sexually-Transmitted Agents," 97th General Meeting of the American Society for Microbiology, C-308, May 4-8, 1997, Miami Beach, USA.

Carrino et al., "Nucleic Acid Amplification Methods," J. Micorbiol. Methods, 1995, 23:3-20.

Check, "Real-time PCR for the rest of us," CAP Today, Jun. 2006, College of American Pathologists, Skokie, IL, USA, 6 pages.

Chemistry Guide, "Automated DNA Sequencing," PE Applied Biosystems, 1998, pp. 1-4~1-6, The Perkin-Elmer Corporation.

Cimino et al., "Post-PCR sterilization: a method to control carry-over contamination for the polymerase chain reaction," Nucleic Acids Res., 1991, 19(1):99-107, Oxford University Press, Oxford, United Kingdom.

Clewley, "Automation of the Polymerase Chain Reaction Part 2. Extraction—the Foundation for Success," Communicable Disease and Public Health, Jun. 1999, 2(2):147-148, Public Health Laboratory Service in association with the Scottish Centre for Infection and Environmental Health, London, United Kingdom.

Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.

(56) References Cited

OTHER PUBLICATIONS

Corrected Request for Inter Partes Reexamination of U.S. Pat. No. 7,482,143, filed on Sep. 14, 2012, 121 pages.

Crotchfelt et al., "Detection of Chlamydia trachomatis by the Gen-Probe Amplified Chlamydia Trachomatis Assay (AMP CT) in Urine Specimens from Men and Women and Endocervical Specimens from Women," J. Clin. Microbiol., Feb. 1998, 36(2):391-394, American Society for Microbiology, Washington D.C., USA.

Davis et al., "Amplification of DNA Using the Polymerase Chain Reaction," in Basic Methods in Molecular Biology, 2nd ed., 1994, p. 121, Appleton & Lange, Norwalk, USA.

Diamandis, "Automation of molecular diagnostics," Clinical Chemistry, 1996, 42:7-8, American Association for Clinical Chemistry, USA.

DiDomenico et al., "Cobas Amplicor™: fully automated RNA and DNA amplification and detection system for routine diagnostic PCR," Clin. Chem., 1996, 42(12):1915-1923, Washington DC American Association for Clinical Chemistry, USA.

Dieffenbach et al., "Setting Up a PCR Laboratory," Genome Rsearch, PCR Methods and Applications, 1993, 3:s2-s7, Cold Spring Harbor Laboratory, Cold Spring Harbor, USA.

Dragon, "Handling Reagents in the PCR Laboratory," Genome Research, PCR Methods and Applications, 1993, 3:s8-s9, Cold Spring Harbor Laboratory, Cold Spring Harbor, USA.

Dynal®, Technical Handbook. Molecular Biology, First Edition. "Dynabeads® biomagnetic separation system," 1992, 4 pages, Dynal AS, Norway.

Erlich, "PCR Technology," in Encyclopedia of Molecular Biology and Molecular Medicine: Mass Spectrometry High Speed DNA Fragment Sizing to Plasma Lipoproteins, vol. 4, 1996, p. 337, VCH Verlagsgesellschaft mbH, Weinheim, Germany.

Espy et al., "Dependence of polymerase chain reaction product inactivation protocols on amplicon length and sequence composition," J. Clin. Microbiol., 1993, 31(9):2361-2365, American Society for Microbiology, Washington D.C., USA.

Farrell, Jr., "RT PCR" in RNA Method: A Laboratory Guide for Isolation and Characterization, 1998, 2nd ed., Chapter 15, pp. 296-307, Academic Press, San Diego, California, USA.

Feinberg, "A Technique for Radiolabeling DNA Restriction Endonuclease Fragments to High Specific Activity", Analytical Biochemistry, 1983, 132:6-13, Academic Press, USA.

Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.

Fiore et al., "The Abbott IMx automated benchtop immunochemistry analyzer system," Clin. Chem., 1988, 34(9):1726-32, American Association for Clinical Chemistry, Washington D.C., USA.

Flexlink(R)®; "TX45E puck handling (mx. 250g),"; located at http://www.flexlink.com/en/offering/conveyor-systems/pallet-and-puck-handling/x45e.jsp; last visited on Jul. 20, 2013; 2 pages.

Friendenberg et al., "Developing a fully automated instrument for molecular diagnostic assays," IVD Technology, 2005, 11(6), 6 pages, A Canon Communications, Los Angeles, USA.

Furrows et al., "'Good laboratory practice' in diagnostic laboratories using nucleic acid amplification methods," Clin. Microbiol. Infect., 2001, 7(5):227-229, Blackwell Science, Oxford, United Kingdom.

Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.

Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA.

Gibson et al., "A homogenous method for genotyping with fluorescence polarization," Clin. Chem., 1997, 43(8):1336-1341, American Association for Clinical Chemistry, Washington D.C., USA.

Gibson et al., "A novel method for real time quantitative RT-PCR," Genome Methods, 1996, 6:995-1001, Cold Spring Harbor Laboratory Press, Cold Spring Harbor, USA.

Giesendorf et al., "Molecular beacons: a new approach for semiautomated mutation analysis," Clin. Chem., 1998, 44(3):482-486, American Association for Clinical Chemistry, Washington D.C., USA.

Gilgen et al., "Hydroxyquinoline overcomes PCR inhibition by UV-damaged mineral oil," Nucleic Acids Res., 1995, 23(19):4001-4002, Oxford University Press, Oxford, United Kingdom.

Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA.

Godfrey-Faussett, "Molecular Diagnosis of Tuberculosis: The Need for New Diagnostic Tools," Thorax, 1995, 50(7):709-711, British Medical Association, London, United Kingdom.

Greenstein, "Preparing and Using M13-Derived Vectors," Current Protocols in Molecular Biology, published 1990, §1.151 and 1.15.4, J. Wiley and Sons, USA.

Haas, "Clinical Instrumentation (General Chemistry and Immunoassay Analyzers)," Anal. Chem., 1993, 65(12):444R-449R, American Chemical Society, Washington D.C., USA.

Haglund et al., "Polymerase Chain Reaction," in Forensic Taphonomy: the Postmortem Fate of Human Remains, 1997, p. 114-115, CRC Press LLC, Boca Raton, USA.

Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.

Hawker, "Laboratory Automation: Total and Subtotal," Clin. Lab. Med., 2007, 27:749-770, Elsevier Health Sciences Division, Philadelphia, USA.

Hawkes et al., "Asymptomatic carriage of Haemophilus ducreyi confirmed by the polymerase chain reaction," J. Genitourin. Med., 1995, 71:224-227.

Hawkins et al., "A Magnetic Attraction to High-Throughput Genomics," Science, 1997, 276:1887 & 1889 (pg. 1888 omitted—advertisement only), Washington, DC: American Association for the Advancement of Science, USA.

Hedrum et al., "Immunomagnetic Recovery of Chlamydia trachomatis from Urine with Subsequent Colorimetric DNA Detection," PCR Methods Appl., 1992, 2:167-171, Cold Spring Harbor Laboratory Press, Cold Spring Harbor, USA.

Heid et al., "Real Time Quantitative PCR," Genome Research, 1996, 6:986-994, Cold Spring Harbor Laboratory Press, Cold Spring Harbor, USA.

Hellyer et al., "Letter to the Editor: Specificity of IS6110-Based Amplification Assays for Mycobacterium tuberculosis Complex," J. Clin. Microbiol., 1997, 35(3):799-801, American Society for Microbiology, Washington D.C., USA.

Herring et al., "ELISA Automation: A Biomek 1000 to Biomek 2000 Comparison of Clinical ELISAs", Application Information, 1995, Beckman Industries, Inc., USA.

Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.

Hicks et al., "Beckman/Sagian "Core" Molecular Biology System,", T-1845A, Beckman Instruments, Inc., 1997, 4 pages.

Higuchi et al., "Simultaneous Amplification and Detection of Specific DNA Sequences," Bio/Technology, 1992, 10:413-417, Nature Publishing Company, New York, USA.

Hildebrandt et al Development of an Automated Sample Preparation Method for HCV, J. Microbiol. Methods, 1997, 30:235-253, Abstract 17, 1 page, Elsevier Biomedical, Amsterdam, Netherlands.

Hill, "Gen-Probe Transcription-Mediated Amplification: System Principles," Jan. 1996, Gen-Probe Incorporated, San Diego, USA, 4 pages.

(56) References Cited

OTHER PUBLICATIONS

Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.

Hill, "Molecular diagnostic testing for infectious diseases using TMA technology," Expert Rev. Mol. Diagn., 2001, 1 (4):445-455, Future Drugs Ltd., London, United Kingdom.

Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.

Hill, "Molecular Diagnostics for Infectious Diseases," J. Clin. Ligand Assay, 1996, 19(1):43-52, Clinical Ligand Assay Society, Wayne, Michigan, USA.

Hoad et al., "Virus Genome Detection by the PCR," in Practical Molecular Virology: Viral Vectors for Gene Expression, 1991, pp. 75-76, Humana Press, Totowa, USA.

Holland et al., "Detection of specific polymerase chain reaction product by utilizing the 5'→3' exonuclease activity of Thermus aquaticus DNA polymerase," Biochemistry, 1991, 88:7276-7280, Proc. Natl. Acad. Sci. USA, Washington D.C., USA.

International Search Report and Written Opinion mailed on Feb. 15, 2013 for PCT Application No. PCT/US2012/063923, 12 pages.

International Search Report and Written Opinion mailed on Feb. 15, 2013 for PCT Application No. PCT/US2012/063914, 9 pages.

International Search Report and Written Opinion mailed on Jun. 12, 2013 for PCT Patent Application No. PCT/US2012/063888, 18 pages.

International Search Report and Written Opinion mailed on Mar. 19, 2013 for PCT Application No. PCT/US2012/063929, 13 pages.

International Search Report and Written Opinion mailed on Dec. 7, 2012 for PCT Patent Application No. PCT/US2011/045107, 18 pages.

International Search Report and Written Opinion mailed on Oct. 4, 2013 for PCT Patent Application No. PCT/US2012/063931, 24 pages.

International Search Report and Written Opinion mailed on Sep. 30, 2013 for PCT Patent Application No. PCT/US2012/063930, 37 pages.

Invitation to Pay Additional Fees mailed on Mar. 1, 2013 for PCT Patent Application No. PCT/US2012/063918, 6 pages.

Invitation to Pay Additional Fees mailed on Mar. 19, 2013 for PCT Patent Application No. PCT/US2012/063930, 8 pages.

Invitation to Pay Additional Fees mailed on Mar. 25, 2013 for PCT Patent Application No. PCT/US2012/063931, 8 pages.

Invitation to Pay Additional Fees mailed on Mar. 6, 2013 for PCT Patent Application No. PCT/US2012/063888, 6 pages.

Invitrogen; Manual, "Dynabeads® DNA Direct™ Blood" Cat. No. 631.02 "For the isolation of PCR-ready genomic DNA from blood" Rev. o. 006, Invitrogen, *Dynal® Invitrogen Bead Separations*, 2007.

Jaklevic, "Automation of High-Throughput PCR Assays," Laboratory Robotics and Automation, 8(5):277-286, John Wiley & Sons Inc., USA.

Jaton et al., "Development of polymerase chain reaction assays for detection of Listeria monocytogenes in clinical cerebrospinal fluid samples," J. Clin. Microbiol., 1992, 30(8):1931-1936, American Society for Microbiology, Washington D.C., USA.

Jungkind et al., "Evaluation of Automated COBAS AMPLICOR PCR System for Detection of Several Infectious Agents and Its Impact on Laboratory Management," J. Clin. Microbiol., 1996, 34(11):2778-2783, American Society for Microbiology, Washington, D.C., USA.

Kalinina et al., "Nanoliter scale PCR with TagMan detection," Nucleic Acids Res., 1997, 25(10):1999-2004, Oxford University Press, Oxford, United Kingdom.

Kapperud et al., "Detection of Pathogenic Yersinia enterocolitica in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA.

Kendrew et al., "Polymerase Chain Reaction," in The Encyclopedia of Molecular Biology, 1994, pp. 864-865, Blackwell Science Ltd., Cambridge, USA.

Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.

Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.

Kolmodin et al., "Basic Principles and Routine Practice," in PCR Cloning Protocols From Molecular Cloning to Genetic Engineering, 1997, pp. 3-5, Humana Press, Totowa, USA.

Kost, G. Chapters J. *Handbook of Clinical Automation, Robotics, and Optimization*;.1, 10, and 12-14; 1996 by John Wiley & Sons, Inc.; 189 pages total.

Kretz et al., "Cycle sequencing," PCR Methods and Applications, 1994, 3:S107-S112, Cold Spring Harbor Laboratory, Cold Spring Harbor Press, USA.

Krieg, "Quantification of RNA by Competitive RT PCR," in a Laboratory Guide to RNA, 1996, p. 210, Wiliey-Liss, New York City, USA.

Kwok et al., "Avoiding False Positive with PCR," Nature, 1989, 339:237-238, Nature Publishing Group, Basingstoke, USA.

Landry, "False-Positive Polymerase Chain Reaction Results in the Diagnosis of Herpes Simplex Encephalitis," J. Infect. Dis., 1995, 172(6):1641-1642, University of Chicago Press, Chicago, USA.

Lay et al., "Real-time fluorescence genotyping of factor V Leiden during rapid-cycle PCR," Clin. Chem., 1997, 43(12):2262-2267, American Association for Clinical Chemistry, Washington D.C., USA.

Lee et al., "Direct Identification of *Vibrio vulmificus* in Clinical Specimens by Nested PCR," J. Clin. Microbial., 1998, 36 (10):2887-2892, American Society for Microbiology, Washington D.C., USA.

Lee et al., "Nucleic Acid Amplification Technologies: Application to Disease Diagnosis," BioTechniques Books, 1997, pp. 1-286, Eaton Publishing, Massachusetts, USA.

Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.

Lisby, "Application of Nucleic Acid Amplification in Clinical Microbiology," in Methods in Molecular Biology: PCR in Bioanalysis, 1998, pp. 1-29, Humana Press, Totowa, USA.

Livak et al., "Oligonucleotides with Fluorescent Dyes at Opposite Ends Provide a Quenched Probe System Useful for Detecting Pcr Product and Nucleic Acid Hybridization," PCR Methods and Applications, 1995, 4:357-362, Cold Spring Harbor Laboratory Press, Cold Spring Harbor, New York, USA.

Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.

Lo, "Setting Up a PCR Laboratory," in Methods in Molecular Medicine: Clinical Applications of PCR, 1998, pp. 12-17, Humana Press, Totowa, USA.

Longo, "Use of uracil DNA glycosylase to control carry-over contamination in polymerase chain reactions" Gene, 1990, 93: 125-128, Elsevier/North-Holland, Amsterdam.

Mabilat et al., "Routine Identification of Mycobacterium Tuberculosis Complex Isolates by Automated Hybridization," J. Clin. Microbiol., 1994, 32(11):2702-2705, American Society for Microbiology, Washington, D.C., USA.

Magnemotion; "MagneMover™ LITE,"; located at http://www.magnemotion.com/industrial-automation/magmoverlite.cfm; last visited on Jul. 20, 2013; 3 pages.

Mangiapan, "Sequence capture-PCR improves detection of mycobacterial DNA in clinical specimens" J Clin Microbiol., 1996, 34: 1209-1215, American Society for Microbiology, USA.

(56) References Cited

OTHER PUBLICATIONS

Martin et al., "PCR and Its Modifications for the Detection of Infectious Disease," Nucleic Acid Amplification Technologies: Application to Disease Diagnosis, 1997, p. 79-100, Eaton Pub. Co., Massachusetts, USA.
McCreedy et al., "Laboratory Design and Work Flow," Diagnostic Molecular Microbiology Principles and Applications, 1993, p. 149-159, Mayo Foundation, Rochester, USA.
Meng et al., "Turbo PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.
Mercier et al., "Direct PCR from whole blood, without DNA extraction," Nucleic Acids Res., 1990, 18(19):5908, Oxford University Press, Oxford, United Kingdom.
Merel et al., "Completely Automated Extraction of DNA from Whole Blood," Clin. Chem., 1996, 42(8):1285-1286, American Association for Clinical Chemistry, USA.
Merel et al., "Perspectives on Molecular Diagnostics Automation," JALA, 2005, 10:342-350, Association for Laboratory Automation, Charlottesville, USA.
Meyers, "PCR Technology," Molecular Biology and Biotechnology: A Comprehensive Desk Reference, 1995, pp. 642-646, VCH Publishers Inc., New York City, USA.
Mischiati et al., "Use of an Automated Laboratory Workstation for Isloation of Genomic DNA Suitable for PCR and Allele-Specific Hybridization," BioTechniques, 1993, 15(1):146-151, Eaton Pub. Co., Natick, USA.
Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.
Mullis, "Eine Nachtfahrt and die Polymerase-Kettenreaktion," Spektrum der Wissenschaft, 1950, pp. 60-67, Germany.
Muramatsu et al., "Molecular Cell Biology Dictionary," 1997, Tokyo Kagaku Dojin Publisher, Tokyo, Japan, English Translation, 10 pages.
Nace, "Automation in Molecular Diagnostics: A Pleasant Surprise," Advance for Medical Laboratory Professionals, 2006, 14(11):64, Merion Publications, King of Prussia, PA, USA.
Nazarenko et al., "A closed tube format for amplification and detection of DNA based on energy transfer," Nucleic Acids Res., 1997, 25(12):2516-2521, Oxford University Press, Oxford, United Kingdom.
Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.
Newton et al., "Instrumentation, Reagents and Consumables," PCR, 1996, 2nd ed., Chpt. 2, pp. 9-28, Bios Scientific, UK.
Nickerson et al., "Automated DNA Diagnostics Using an ELISA-based Oligonucleotide Ligation Assay," Proc. Natl. Acad. Sci. USA, 1990, 87:8923-8927, National Academy of Sciences, Washington, D.C., USA.
Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.
Noordhoek et al., "Reliability of Nucleic Acid Amplification for Detection of Mycobacterium Tuberculosis: an International Collaborative Quality Control Study Among 30 Laboratories," J. Clin. Microbiol., 1996, 34(10):2522-2524, American Society for Microbiology, Washington D.C., USA.
Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.
Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA.
Olive, "Q-Beta Replicase Assays for the Clinical Detection of Infectious Agents," in Nucleic Acid Amplification Technologies: Application to Disease Diagnosis, 1997, p. 110, Eaton Pub. Co., Natick, USA.
Olsvik et al., "Magnetic Separation Techniques in Diagnostic Microbiology," Clin. Microbiol. Rev., 1994, 7(1):43-54, American Society for Microbiology, Washington, D.C., USA.
Oste, "Polymerase Chain Reaction," Product Application FOCUS, BioTechniques, 1988, 6(2):162-167, Informa Healthcare USA, Inc., UK.
Package Insert, "APTIMA® Assay for *Neisseria gonorrhoeae*," IN0148-01-REG, Rev. 1, Nov. 2004, Gen-Probe Incorporated, San Diego, USA, 20 pages.
Package Insert, "APTIMA® HCV RNA Qualitative Assay," 500237 Rev. B, Jul. 2006, Gen-Probe Incorporated, San Diego, USA, 18 pages.
Package Insert, "Gen-Probe® Amplified Mycobacterium Tuberculosis Direct Test," IN0006 Rev. A, Feb. 24, 1994, Gen-Probe Incorporated, San Diego, USA, 14 pages.
Package Insert, "Gen-Probe® AMPLIFIED™ Chlamydia Trachomatis Assay," IN0012 Rev. A, Jan. 6, 1997, Gen-Probe Incorporated, San Diego, USA, 17 pages.
Package Insert, "Gen-Probe® AMPLIFIED™ Chlamydia Trachomatis Swab Specimen Preparation Kit," In0016 Rev. A, Jan. 6, 1997, Gen-Probe Incorporated, San Diego, USA, 3 pages.
Package Insert, "Gen-Probe® AMPLIFIED™ Chlamydia Trachomatis Urine Specimen Preparation Kit," IN0017 Rev. A, Nov. 11, 1996, Gen-Probe Incorporated, San Diego, USA, 3 pages.
Package Insert, "Gen-Probe® APTIMA® Combo 2 Assay," IN0037 Rev. A, Jun. 6, 2001, Gen-Probe Incorporated, San Diego, USA, 28 pages.
Package Insert, "Gen-Probe® APTIMA Combo 2@ Assay," 501011 Rev. A, Jan. 2007, Gen-Probe Incorporated, San Diego, USA, 44 pages.
Package Insert, "Gen-Probe® APTIMA® Assay for *Chlamydia trachomatis*," IN0147-01, Rev. B, Apr. 2005, Gen-Probe Incorporated, San Diego, USA, 24 pages.
Package Insert, "Procleix® HIV-1/HCV Assay," IN0076-01-FDA, Rev. 3, Jun. 2004, Gen-Probe Incorporated, San Diego, USA, 28 pages.
Package Insert, "Procleix® HIV-1/HCV Assay," IN0076-02-FDA, Rev. 1, Jan. 2005, Gen-Probe Incorporated, San Diego, USA., 32 pages.
Package Insert, "Procleix® Ultrio™ Assay," IN0167EN, Rev. 1, Aug. 2004, Gen-Probe Incorporated, San Diego, USA, 44 pages.
Package Insert, "Procleix@ WNV Assay," IN0155, Rev. 1, Apr. 2004, Gen-Probe Incorporated, San Diego, USA, 15 pages.
Paillard et al., "Direct nucleic acid diagnostic tests for bacterial infectious diseases: *Streptococcal pharyngitis*, pulmonary tuberculosis, vaginitis, chlamydial and gonococcal infections," MLO, Jan. 2004, pp. 10-15, Medical Laboratory Observer, NP Communications, LLC, Monroe Township, USA.
Panaccio et al., "PCR based diagnosis in the presence of 8% (v/v) blood," Nucleic Acids Res., 1991, 19(5):1151, Oxford University Press, Oxford, United Kingdom.
Patel et al., "Death from Inappropriate Therapy for Lyme Disease," Clin. Infect. Dis., 2000, 31:1107-1109, The University of Chicago Press, Chicago, USA.
Patterson et al., "Random and continuous-access immunoassays with chemiluminescent detection by Access automated analyzer," Clin. Chem., 1994, 40(11):2042-2045, American Association for Clinical Chemistry, Washington D.C., USA.
Pauwels et al., "Automated techniques in biotechnology," Current Opinion in Biotechnology, 1995, 6:111-117, Current Biology Ltd., London, United Kingdom.
Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.
Persing, "Diagnostic molecular microbiology. Current challenges and future directions," Diagn. Microbiol. Infect. Dis., 1993, 16(2):159-163, Elsevier Biomedical, New York, USA.

(56) References Cited

OTHER PUBLICATIONS

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.
Request for Inter Partes Reexamination of U.S. Pat. No. 7,524,652, filed on Sep. 15, 2012, 134 pages.
Riggio et al., "Identification by PCR of Helicobacter pylori in subgingival plaque of adult periodontitis patients," J. Med. Microbiol., 1999, 48:317-322, The Pathological Society of Great Britain and Ireland.
Rosenblum et al., "New dye-labeled terminators for improved DNA sequencing patterns," Nucleic Acids Res., 1997, 25(22):4500-4504, Oxford University Press, UK.
Rudi et al., "Rapid, Universal Method to Isolate PCR-Ready DNA Using Magnetic Beads," BioTechniques, 1997, 22(3):506-511, Informa Healthcare USA, Inc., UK.
Rudi, et al., "Detection of Toxin-Producing Cyanobacteria by Use of Paramagnetic Beads for Cell Concentration and DNA Purification," 1998, Appl. Environ. Microbiol., 64(1):34-37, Am. Society of Microbiol., USA.
Schepetiuk et al., "Detection of *Chlamydia trachomatis* in Urine Samples by Nucleic Acid Tests: Comparison with Culture and Enzyme Immunoassay of Genital Swab Specimens," J. Clin Micorbiol., Dec. 1997, 35(12):3355-3357.
Skeggs, "An automatic method for colorimetric analysis," Am. J. Clin. Pathol., 1957, 28:311-322, American Society of Clinical Pathologists, Chicago, USA.
Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.
Smith et al., "Detection of *Mycobacterium tuberculosis* Directly from Sputum by Using a Prototype Automated Q-Beta Replicase Assay," J. Clin. Microbiol., 1997, 35(6):1477-1483, American Society for Microbiology, Washington, D.C., USA.
Smith et al., "Performance of an Automated Q-Beta Replicase Amplification Assay for Mycobacterium tuberculosis in a Clinical Trial," J. Clin. Microbiol., 1997, 35(6):1484-1491, Am. Society for Microbiology, USA.
Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.
Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.
Stone et al., "Detection of rRNA from four respiratory pathogens using an automated Qβ replicase assay," Mol. Cell. Probes, 1996, 10:359-370, Academic Press Limited, San Diego, California, USA.
Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.
Sutton et al., "Hands Free Polymerase Chain Reaction," International Symposium on Laboratory Automation and Robotics, Oct. 17-20, 1993, p. 326-336, Boston, USA.
Sutton et al., "PCR Has Outgrown Appropriate Automated Instrumentation But Help is on the Way," Today's Chemist at Work, 1995, p. 42-48, American Chemical Society, Washington, D.C., USA.
Taos Inc. "TCS230 Programmable Color to Light-to-Frequency Converter," www.http?pdfl.alldatasheet.com/datasheet-pdf/view/96470/ETC/TCS230.html: Jan. 31, 2003, pp. 1-8.
Techne PHC-3 Thermal Cycler—Techni, Jun. 2009, Pegasus Scientific Inc., USA.

Tjian, "Purification and comparative properties of the delta and sigma subunits of RNA polymerase from *Bacillus subtilis*" Eur. J. Biochem., 1977, 74:149, Blackwell Science Ltd. on behalf of the Federation of European Biochemical Societies, UK.
Tyagi et al., "Extremely sensitive, background-free gene detection using binary proves and QB Replicase," Biochemistry, 1996, 93:5395-5400, Proc. Natl. Acad. Sci. USA, Washington D.C., USA.
Tyagi et al., "Molecular Beacons: Probes that Fluoresce upon Hybridization," Nature Biotechnology, 1996, 14:303-308, Nature Publishing Company, New York, USA.
Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA.
Van Gemen, Accuract B. at al.; "The One-tube Quantitative HIV-1 RNA NASBA: Precision, and Application,"; 1995; PCR Methods Appl.; vol. 4; pp. 177-184.
Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.
Voss et al., "Direct genomic fluorescent on-line sequencing and analysis using in vitro amplification of DNA," Nucl. Acids Res., 1989, 17(7):2517-2527, IRL Press, USA.
Walker et al., "Detection of *Mycobacterium tuberculosis* DNA with thermophilic strand displacement amplification and fluorescence polarization," Clin. Chem., 1996, 42(10):1604-1608, American Association for Clinical Chemistry, Washington D.C., USA.
Walker et al., "Strand displacement amplification (SDA) and transient-state fluorescence polarization detection of Mycobacterium tuberculosis DNA," Clin. Chem., 1996, 42(1):9-13, American Association for Clinical Chemistry, Washington D.C., USA.
Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA.
Whelan et al., "The Role of Nucleic Acid Amplification and Detection in the Clinical Microbiology Laboratory," Annu. Rev. Microbiol., 1996, 50:349-373, Annual Reviews, Palo Alto, USA.
Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.
Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.
Wittwer et al., "The LightCycler: a microvolume multisample fluorimeter with rapid temperature control," BioTechniques, 1997, 22:176-181, Informa Healthcare USA, Inc., London, United Kingdom.
Yourno et al., "A method for nested PCR with single closed reaction tubes," PCR Methods Appl., 1992, 2(1):60-65, Cold Spring Harbor Laboratory Press, Cold Spring Harbor, New York, USA.
Genprobe; "Test Procedure Guide. Amplified Mycobacterium Tuberculosis Direct (MTD) Test,"; 2000, 1 page.
International Search Report and Written Opinion mailed on Nov. 6, 2013 for PCT Patent Application No. PCT/US2012/063918, 22 pages.
ABI Product Catalogue, 1993-1994, "DNA Sequencing Reagents," p. 146, Applied Biosystems, USA.
Anonymous, "GeneAmp optical reaction plate," Nature, 1998, 391(8):210, Nature Publishing Group, USA.
Asper et al., "Laboratory Mechanization and Automation," in Laboratory Organization Automation, 1991, pp. 271-275, Walter deGruyter, USA.
Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.
Billyard, et al., "Early detection of HIV-1 RNA from sero-conversion panels using Gen-Probe's transcription-mediated amplifica-

(56) References Cited

OTHER PUBLICATIONS tion," The San Diego Conference Nucleic Acid Technology: The Cutting Edge of Discovery, Nov. 6-8, 1997, Clin. Chem., 1997, 43(11):2221, Am. Assoc. for Clin. Chem., USA.
Burg et al., "Real-time fluorescence detection of RNA amplified by Q beta replicase," Anal. Biochem., 1995, 230(2):263-272, Academic Press, Orlando, Florida, USA.
Chemistry Guide, "ABI Prism DNA Sequencing," 1995, pp. 1-3-1-6, The Perkin-Elmer Corporation, USA.
Civitello et al., "A simple protocol for the automation of DNA cycle sequencing reactions and polymerase chain reactions," DNA Sequence—J. DNA Sequencing and Mapping, 1992, 3:17-23, Harwood Academic Publishers GmbH, UK.
Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.
Educational Guide, "New Directions in Molecular Diagnostic Testing," pp. 1-12, Rev. A, 2000, Gen-Probe Incorporated, San Diego, USA.
Felder, "Automation of Preanalytical Processing and Mobile Robotics," in Handbook of Clinical Automation, Robotics, and Optimization, 1996, pp. 252-256, John Wiley & Sons, Inc., USA.
Hawkins et al., "Thermal Cycle DNA Sequence Setup Using a Modified Lab Workstation," LRA, 1995, 7:117-122, VCH Publishers, New York City, USA.
Higuchi et al., "Kinetic PCR Analysis: Real-time Monitoring of DNA Amplification Reactions," Bio/Technology, 1993, 11(9):1026-30, Nature Publishing Group, New York, USA.
Hill et al., "The Polymerase Chain Reaction in Molecular and Micro-biology," Biotechnol. Genet. Eng. Rev., 1992, 10:343-377, Taylor & Francis, UK.
Holmberg et al., "Automatic Preparation of DNA Templates for Sequencing on the ABI Catalyst Robotic Workstation," Automated DNA Sequencing and Analysis, 1994, Academic Press Inc., San Diego, USA.
Hunkapiller, "Advances in DNA sequencing technology," Curr. Opin. Genet. Dev., 1991, 1:88-92, Elsevier, UK.
Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.
Kasper, "Automated Instrumentation (Generic)," in Clinical Laboratory Instrumentation and Automation: Principles, Applications, and Selection, 1994, pp. 184-205, W.B. Saunders Company, USA.
Kaufman et al., "Direct Sequencing by PCR," in Handbook of Molecular and Cellular Methods in Biology and Medicine, 1995, pp. 233-235, CRC Press, USA.
Krieg, ed., "Quantitation of RNA Transcripts Using RT-PCR," in a Laboratory Guide to RNA: Isolation, Analysis, and Synthesis, 1996, pp. 176-190, John Wiley & Sons, Inc., USA.
Little et al., "Recent Advances in Robotic Automation of Microplate Assays," Lab. Info. Mgmt., 1994, 26:89-99, Elsevier Science, Amsterdam, Netherlands.
Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.
Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.
McDonough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.
Mertes et al., Automatische genetische Analytik, 1997, forward and pp. 68, 69, 73 & 74, Wiley-VCH, Germany; German Language Reference.
Mizutani et al., "Magnetic Separation in Molecular Studies of Human Leukemia," in Advances in Biomagnetic Separation, 1994, p. 127-133, Eaton Publishing, USA.
Olsvik et al., "Magnetic Separation in Laboratory Diagnosis of Infectious Diseases," in Advances in Biomagnetic Separation, 1994, pp. 149-158, Eaton Publishing, USA.
Olympus Corporation, "Olympus News Release: Automated Chemistry Analyser AU1000," 1997, http://www.olympus-global.com/en/news/1997a/nr970421au1000e.jsp, downloaded Jun. 17, 2013, USA, 3 pages.
Overbergh et al., "Quantification of Murine Cytokine mRNAs Using Real Time Quantitative Reverse Transcriptase PCR," Cytokine, 1999, 11(4):305-312, Academic Press, USA.
Petrik et al., "High throughput PCR detection of HCV based on semiautomated multisample RNA capture," J. Virol. Methods, 1997, 64:147-159, Elsevier/North-Holland Biomedical Press, Amsterdam, Netherlands.
Piatek et al., "Molecular beacon sequence analysis for detecting drug resistance in Mycobacterium tuberculosis," Nature Biotechnology, 1998, 16:359-363, Nature America Publishing, New York, USA.
Shah et al., "Novel, Ultrasensitive, Q-Beta Replicase-Amplified Hybridization Assay for Detection of Chlamydia trachomatis," J. Clin. Microbiol., 1994, 32(11):2718-2724, American Society for Microbiology, USA.
Slatko, "Thermal Cycle Dideoxy DNA Sequencing," in Protocols for Gene Analysis (Methods in Molecular Biology), 1994, vol. 31, pp. 35-45, Humana Press Inc., USA.
Sloan et al., "Screening Yeast Artificial Chromosome Libraries with Robot-Aided Automation," GATA, 1993, 10(6):128-143, Elsevier Science Publishing Co., Inc., USA.
Truchaud et al., "Liquid-Phase Reactions Started by Rehydrating Lyophilized Reagents in a Centrifugal Analyzer," Clin. Chem., 1985, 31(9):1506-1508, Am. Assoc. for Clin. Chem., USA.
Tyagi et al., "Multicolor molecular beacons for allele discrimination," Nat. Biotechnol., 1998, 16:49-53, Nature Publishing Group, USA.
Vonderschmitt, ed., "Robots in the Clinical Laboratory," in Laboratory Automation Organization, 1991, pp. 576-577, Walter deGruyter, USA.
Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.
Webster's New World Dictionary, Third college Edition, 1988: Definition of Incubate, Incubator.
Yohda et al., "Development of a Novel Laboratory Automation System for Molecular Biology," Kaguku-Koguku Symposium, 1998, p. 17-20.
Muller et al., "Evaluation des klinish-chemischen Analysensystems Technicon DAX 72," Lab. Med., 1992, 16:210-218, Am. Soc. For Clinical Pathology, USA, with English Sumarry.
First Chinese Office Action mailed on May 4, 2015 for CN Patent Application No. 201280066155.4, English Translation, 16 pages.
International Search Report and Written Opinion mailed on Aug. 9, 2012 for PCT Patent Application No. PCT/US2012/037585, 10 pages.

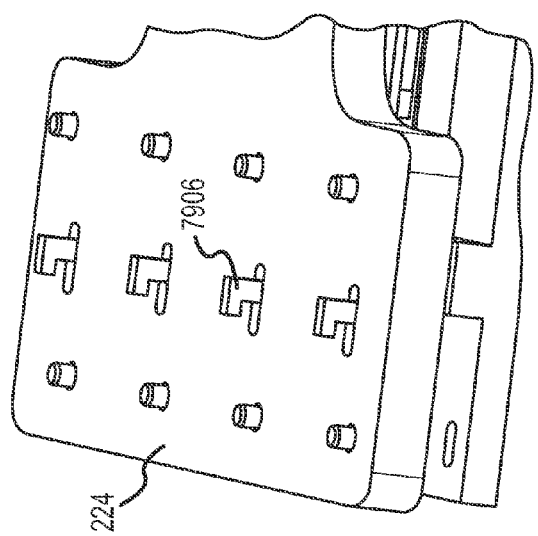
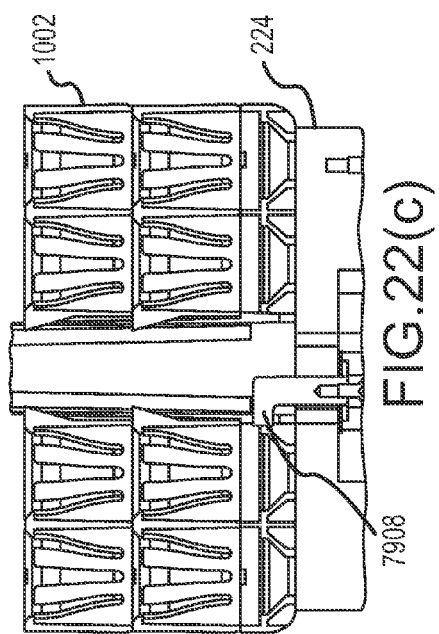
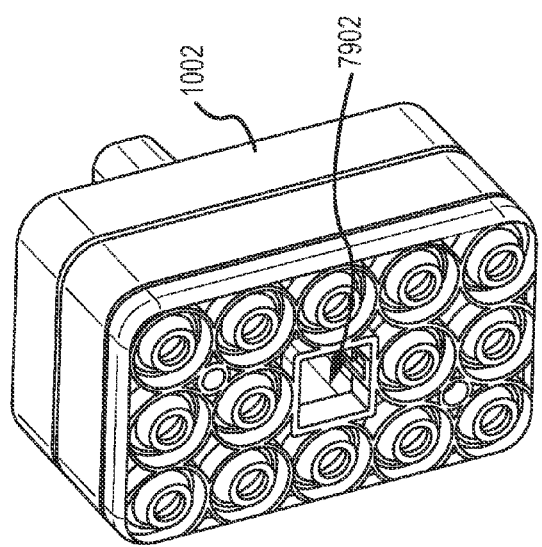
FIG.22(a)
FIG.22(b)
FIG.22(c)

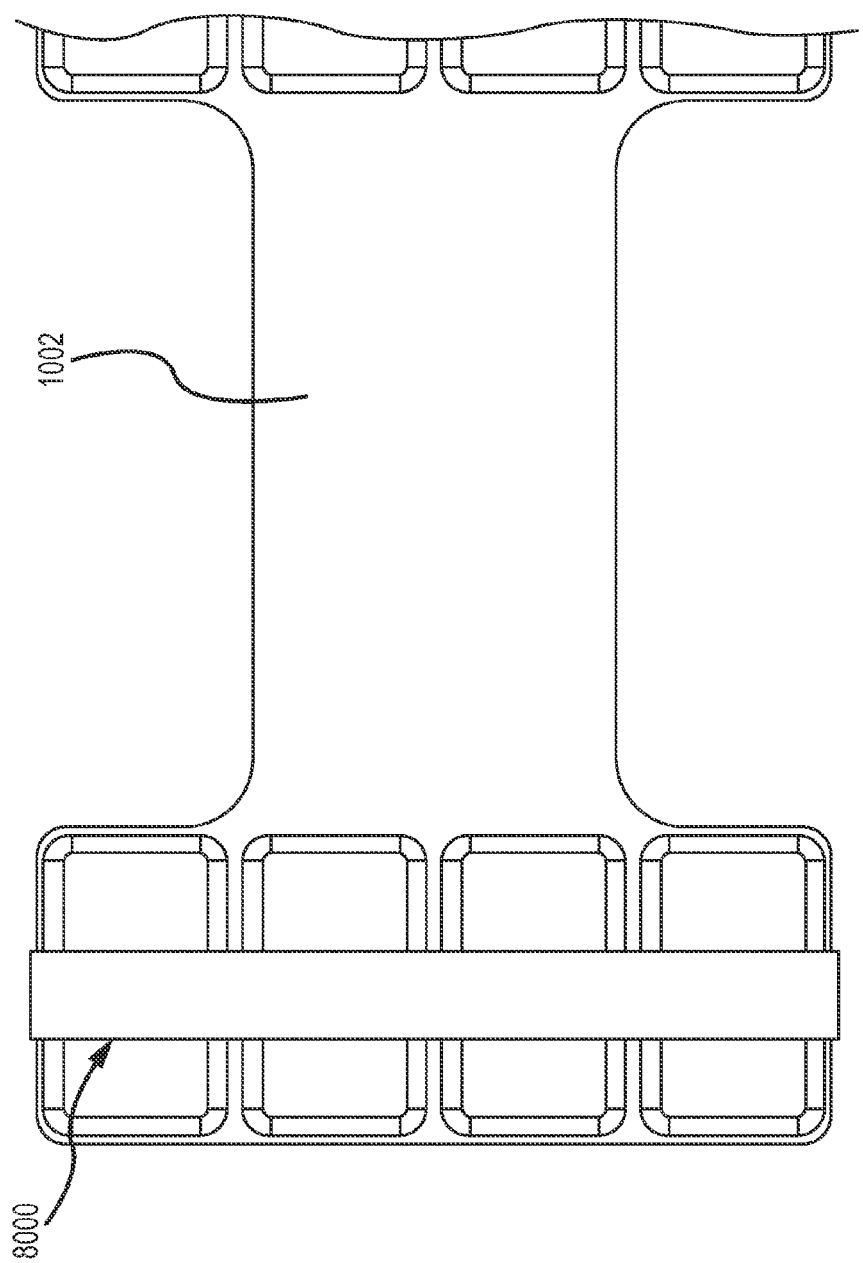

CENTRIFUGE SYSTEM AND WORKFLOW

CROSS-REFERENCES TO RELATED APPLICATIONS

The sequence continues with a previously emptied centrifuge adapter moved by centrifuge adapter gripper 227 from shuttle position G to shuttle position F. A previously spun centrifuge adapter is moved by centrifuge adapter gripper 227 from area H of centrifuge 206 to the vacant space on shuttle position G. An adapter loaded with samples that have not been centrifuged is moved by centrifuge adapter gripper 227 from shuttle I to the area H of the centrifuge 206.

BACKGROUND

The centrifuge can be loaded according to the following sequence. A first sample tube with a highest centrifugation priority can be identified by the scheduler in the distribution area 204. Adapter A1 (1708) can be loaded with the first sample tube from distribution area 204 in a position closest to the center position of adapter A1 (1708). A second sample tube with comparable weight to the first sample tube can be selected by the scheduler from distribution area 204 and loaded into a position of A3 (1712) that is the same position occupied by the first sample tube in A1 (1708). A sample tube with the second highest centrifugation priority is identified by the scheduler in distribution area 204 to be the third sample tube. The third sample tube is loaded into a position in adapter A2 (1710) that is closest to the center of A2 (1710). A fourth sample tube with comparable weight to the third sample tube can be selected by the scheduler from distribution area 204 and loaded into a position of A4 (1714) that is the same position occupied by the third sample tube in A2 (1710). The process continues with filling open positions in the adapters A1-A4 (1708-1714) with a first sample tube, a second sample tube, a third sample tube and a fourth sample tube, as described above, to fill the positions indicated in at begin load pattern 1700, then the positions indicated in yellow (1702) at 1702, then the positions indicated at 1704, and then the positions indicated at last load pattern 1706, until all adapters are filled. In some embodiments, if a centrifuge cycle is nearing completion (e.g., within 30 seconds of completion), the loading of adapters may halt before all adapters are filled and the centrifuge may be loaded with adapters that have not been filled to capacity.

Medical specimens may require centrifuging before analysis can be performed. A centrifuge may have one or more buckets capable of receiving a centrifuge adapter. A centrifuge adapter is a tray that can receive multiple specimen containers. Centrifuge imbalance may occur when centrifuge adapters are loaded unevenly. The weights of specimen containers to be inserted into centrifuge adapters may be used in determining how to balance centrifuge adapters.

A centrifuge may be mounted on a drawer to allow improved access to the centrifuge. However, centrifuge operation may be impeded or the centrifuge may be damaged if the centrifuge is operated when the drawer is partially or fully extended. Additionally, cables required for the operation of the centrifuge may be damaged by the operation of the drawer if they become entangled in components of the drawer.

Embodiments of the invention address these and other problems, individually and collectively.

BRIEF SUMMARY

Embodiments of the technology relate to systems and methods for efficiently processing patient samples.

A first embodiment is directed to a method for loading specimen containers into centrifuge adapters. A first specimen container gripper loads a plurality of specimen containers into a centrifuge adapter. The first specimen container gripper sequentially loads single specimen containers of the plurality of specimen containers into the centrifuge adapter until the plurality of specimen containers are loaded. The centrifuge adapter is transported to a centrifuge area by an adapter shuttle. A centrifuge adapter gripper transports the centrifuge adapter into a centrifuge. The centrifuge centrifuges the centrifuge adapter. The centrifuge adapter gripper transports the centrifuge adapter from the centrifuge to an adapter shuttle. A second specimen container gripper unloads the plurality of specimen containers from the centrifuge adapter. The second specimen container gripper sequentially unloads single specimen containers of the plurality of specimen containers until the plurality of specimen containers are unloaded.

In another embodiment, a method for replacing a set of centrifuged adapters with a set of uncentrifuged adapters is described. A centrifuge adapter gripper transports a first centrifuge adapter from which all specimen containers have been removed to a temporary holding area. The centrifuge adapter gripper transports a second centrifuge adapter containing previously centrifuged sample containers from a centrifuge to a first shuttle position. The centrifuge adapter gripper transports a third centrifuge adapter containing sample containers that have not been centrifuged from a second shuttle position to a centrifuge. The centrifuge adapter gripper transports a fourth centrifuge adapter from a temporary holding area to a second shuttle position, wherein the centrifuge adapter contains sample containers that have not been centrifuged.

In a further embodiment, a method for loading specimen containers into a set of centrifuge adapters is described. A specimen container gripper loads a first specimen container that is first in a sequential order into a first position of a first centrifuge adapter. The first position of the first centrifuge adapter is one of a first set of positions that are within a first distance from the center of the first centrifuge adapter. A specimen container gripper loads a second specimen container that is second in the sequential order into a first position of a second centrifuge adapter. The first position of the second centrifuge adapter is in a first set of positions that are within a first distance from the center of the second centrifuge adapter. A specimen container gripper a third specimen container that is third in the sequential order into a first position of a third centrifuge adapter. The first position of the third centrifuge adapter is in a first set of positions that are within a first distance from the center of the third centrifuge adapter. A specimen container gripper loads a fourth specimen container that is fourth in the sequential order into a first position of a fourth centrifuge adapter. The first position of the fourth centrifuge adapter is in a first set of positions that within a first distance from the center of the fourth centrifuge adapter. When all of the first set of positions that are within a first distance from the center of the first centrifuge adapter are filled, all of the first set of positions that are within a first distance from the center of the second centrifuge adapter are filled, all of the first set of positions that are within a first distance from the third centrifuge adapter are filled, and all of the first set of positions that are within a first distance from the center of the fourth centrifuge adapter are filled, a specimen container gripper loads a fifth specimen container into a second position of a first centrifuge adapter. The second position of the first centrifuge adapter is one of a second set of positions that are not within a first distance from the center of the first centrifuge adapter. The fifth specimen container follows a previously loaded specimen container in the sequential order. A specimen container gripper loads a sixth specimen container into a second position of a second centrifuge adapter. The second position of the second centrifuge adapter is one of a second set of positions that are not within a first distance from the center of the second centrifuge adapter. The sixth specimen container follows a previously loaded specimen container in the sequential order. A specimen container gripper loads a seventh specimen container into a second position of a third centrifuge adapter. The second position of the third centrifuge adapter is one of a second set of positions that are not within a first distance from the center of the third centrifuge adapter, wherein the seventh specimen container follows a previously loaded specimen container in the sequential order. A specimen container gripper loads an eighth specimen container into a second position of a fourth centrifuge adapter. The second position of the fourth centrifuge adapter is one of a second set of positions that are not within a first distance from the center of the fourth centrifuge adapter. The eighth specimen container follows a previously loaded specimen container in the sequential order.

Another embodiment is directed to a centrifuge drawer. The centrifuge drawer includes a platform coupled to a frame via telescoping rails. The platform is configured to support a centrifuge. The centrifuge drawer also includes a latch coupled to the platform.

An additional embodiment is directed to a method for installing a centrifuge in centrifuge drawer. The method includes applying a loading tool to a centrifuge. The loading tool includes a plurality of jacks and a plurality of wheels. The centrifuge is lifted by extending the plurality of jacks. The centrifuge is rolled to a position over centrifuge drawer using the plurality of wheels. The plurality of jacks is retracted until the centrifuge is supported by the centrifuge drawer. The loading tool is then removed from the centrifuge.

In a first embodiment directed to a tubular holder of a centrifuge adapter, a first end of the tubular holder is coupled to the centrifuge adapter and a second end of the tubular holder has an opening configured to receive a bolt. The tubular holder includes a first vertical groove on the interior of the tubular holder. The first vertical groove terminates at the opening of the tubular holder. The tubular holder also includes a second vertical groove on the interior of the tubular holder. The second vertical groove terminates at the opening of the tubular holder. The tubular holder also includes a first horizontal groove of the tubular holder. The first horizontal groove connects with the first vertical groove such that a first pin can enter the tubular holder via the first vertical groove and the first pin can travel from the first vertical groove into the first horizontal groove. The tubular holder also includes a second horizontal groove of the tubular holder. The second horizontal groove connects with the first vertical groove such that a second pin can enter the tubular holder via the second vertical groove and the second pin can travel from the second vertical groove into the second horizontal groove. The first pin and the second pin are coupled to the bolt and the bolt is coupled to a robotic arm.

In a second embodiment directed to a tubular holder of a centrifuge adapter a first end of the tubular holder is coupled to the centrifuge adapter and a second end of the tubular holder has an opening configured to receive a bolt. A first pin and a second are coupled to the bolt. The opening has a keyhole shape configured to match a cross-sectional profile of the bolt having the first pin and the second pin. The tubular holder includes a first vertical groove on the interior of the tubular holder. A first end of the first vertical groove terminates at the opening of the tubular holder and a second end of the first vertical groove terminates at a shelf. A first end of the second vertical groove terminates at the opening of the tubular holder and a second end of the second vertical groove terminates at the shelf. The shelf has a first notch and a second notch. The first vertical groove is configured to receive the first pin and the second vertical groove is configured to receive the second pin when the bolt descends through the opening of the tubular holder. the first notch is configured to receive the first pin and the second notch is configured to receive the second pin after the bolt has descended such that the first pin and the second pin are below the shelf and after the bolt has rotated such that first pin aligns with the first notch and the second pin aligns with the second notch.

In another embodiment, a method for gripping a centrifuge adapter is described. A bolt coupled to the robot arm is inserted by the downward movement of a robotic arm into a tubular holder coupled to a centrifuge adapter. The robot arm rotates the bolt with respect to the tubular holder. The bolt then enters a locking position within the tubular holder. The robotic arm lifts the centrifuge adapter until the upper surface of the tubular holder contacts the lower surface of the housing of the robotic arm. The contact between the tubular holder and the robot arm damps movement of the centrifuge adapter with respect to the robot arm.

In an additional embodiment, a first embodiment of centrifuge adapter shuttle is described. One or more hooks are movably coupled to the centrifuge adapter shuttle. The hooks are configured to mate with one or more openings in a centrifuge adapter. After a centrifuge adapter is loaded onto a centrifuge adapter shuttle, the hooks are moved laterally such that the hooks overhang a ledge of the openings. In this manner, the centrifuge adapter is restrained from being lifted away from the centrifuge adapter shuttle.

In a further embodiment, a second embodiment of a centrifuge adapter shuttle is described. The centrifuge adapter shuttle includes a controller, a power supply communicatively coupled to the controller, and an electromagnet mechanically coupled to a centrifuge adapter shuttle. The electromagnet receives power from the power supply. After a centrifuge adapter is loaded onto a centrifuge adapter shuttle, power is supplied to the electromagnet such that the electromagnet electromagnetically couples to a metal bar that is coupled to the centrifuge adapter.

These and other embodiments of the technology are described in further detail below.

BRIEF DESCRIPTION OF THE DRAWINGS

A further understanding of the nature and advantages of the different embodiments may be realized by reference to the following drawings.

FIGS. 22(a)-(c) show an illustrative centrifuge adapter lift-up prevention device, according to a first embodiment.

FIG. 23 shows an illustrative centrifuge adapter lift-up prevention device, according to a second embodiment.

DETAILED DESCRIPTION

Figure 1:
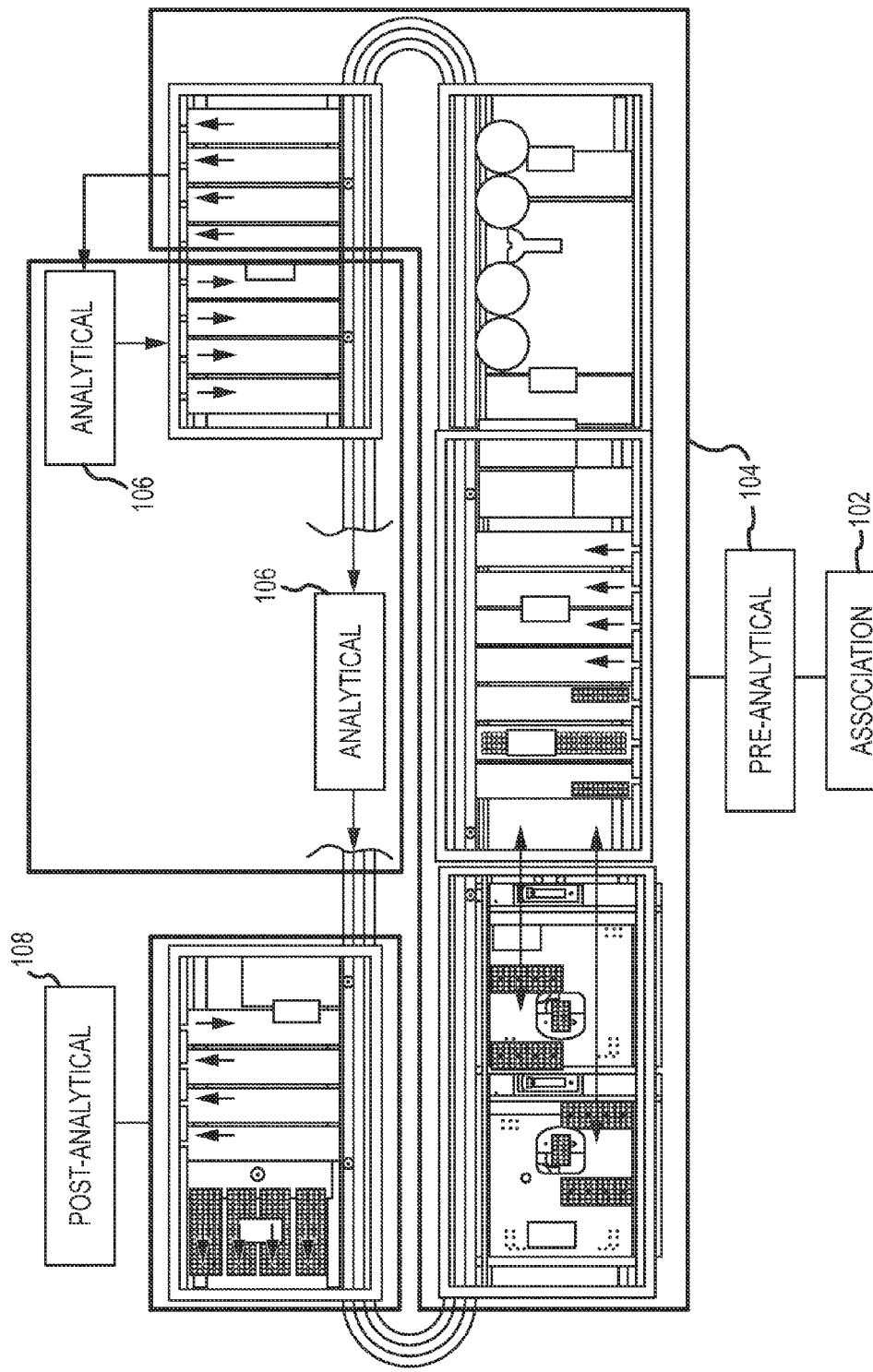
FIG. 1 depicts a block diagram of components associated with phases of a laboratory automation system.

Embodiments of the present technology relate to an analytical medical laboratory system and method for processing medical specimens. These embodiments, as will be described in more detail below, are advantageous because they provide, among other advantages, greater speed, accuracy, efficiency, and prevention of contamination. As discussed above, many conventional laboratory systems may have a process that uses standalone units throughout the lab, requiring that specimens be manually transported between each standalone unit, while others may connect some of the units with a conveyance system to move the specimens from unit to unit. Additionally, as discussed above, sample tube sizes and equipment from different manufacturers may be constraints in conventional laboratory systems.

The laboratory system can operate a controlled process using a central controller or scheduler. By keeping the samples under the control of an intelligent scheduler, the system may provide efficient usage of every instrument. The system can maintain a consistent minimal turnaround time and maximize the throughput of the entire system by maintaining control of the process and only delivering samples to instruments when those instruments are ready and available.

In embodiments of the invention, a sample can be contained in a specimen container and processed by a laboratory automation system. A "specimen container," also referred to as a "sample container," "sample tube," and "tube," may have any suitable shape or form. In some embodiments, the specimen container may be in the form of a sample tube. An exemplary specimen container may be a sample tube with a closed bottom end and an open top end. Some sample tubes have an aspect ratio of 3:1 or greater. Specimen containers may be made of any suitable material including plastic, glass, etc. A cap that is structured to cover and attach to the open end of the sample tube body may be used with a sample tube.

In embodiments of the invention, one or more specimen containers may be inserted into a "sample carrier" (also referred to as a "carrier" or a "sample container holder") for transport. A sample carrier may hold the one or more specimen containers in an upright position and provide stability as the carrier is transported along a conveyance system. In some embodiments, a sample carrier may be a puck or a cylindrical receptacle configured to receive a single specimen container. The sample carrier may have vertical slits to allow the contents of a specimen container to be viewed and analyzed. In some cases, the sample carrier may be in the form of a sample tube rack with an array of recesses for receiving specimen containers.

The laboratory system may further utilize one or more robotic gripper units mounted on robotic arms. Each robotic arm unit can have a robotic gripper for gripping sample tubes and may be equipped with one or more means for detecting information about sample tubes. The terms "gripper" and "robotic gripper" are used interchangeably herein. The means for detecting information about a sample tube may include a first imaging device, such as a camera, for identifying a sample tube among a plurality of sample tubes in a rack. The identified sample tube is gripped by the gripper. The means for detecting information about sample tubes may further include a second imaging device to obtain an image of the gripped sample tube. The level of liquid in the sample tube may be determined from the image obtained by the second imaging device or from a transmission measurement using emitter and receiver units coupled to the robotic arm unit. In comparison with prior art systems, which have a camera mounted on a track and thus require all sample tubes to be on the track before the tubes can be identified, the laboratory system described herein can identify a sample tube before it is placed on a conveyer track. As a result, samples that do not need to be transported on the conveyer are not placed on the conveyer merely for the purpose of sample tube identification. Further, urgent samples can have a prioritized placement on the conveyer track.

Use of a plurality of robotic gripper units in the laboratory system can also increase sample processing efficiency. An input module gripper can identify a sample tube and make data measurements as described above. After the input module gripper delivers the sample tube to a distribution area, a distribution area gripper (e.g., a first specimen container gripper) can deliver a sample tube to a subsequent module such as a centrifuge module or conveyor. For example, the distribution area gripper may load sample tubes into a centrifuge adapter. In the centrifuge module, a centrifuge tube gripper (e.g., a second specimen container gripper) can be used to, e.g., transport sample tubes, place sample tubes in centrifuge adapters, and/or unload sample tubes from centrifuge adapters. A centrifuge adapter gripper can be used to transport centrifuge adapters. The use of multiple grippers may increase processing efficiency relative to prior art systems that use a single gripper to transport sample tubes and centrifuge adapters.

FIG. 1 depicts one embodiment of a medical laboratory system for processing patient samples. The laboratory system includes components associated with association phase 102, pre-analytical phase 104, analytical phase 106, and post-analytical phase 108.

The pre-analytical phase 104 can include preparing patient samples for analysis. During the pre-analytical phase 104, the patient and test information can be deciphered, the process for analysis can be planned, quality checks may be performed, the sample may be separated into its constituent components (e.g., centrifuged), the sample may be divided into multiple specimen containers (e.g., aliquotted), and/or the sample can be delivered to one or more analyzers and/or racks. The pre-analytical phase 104 can manage the flow of samples to different instruments and different analyzers within the lab system. This process management may permit the system to operate efficiently and with minimal instruments. Additionally, scheduling that occurs during the pre-analytical phase 104 enables efficient processing of samples.

Embodiments of the system can identify the patient samples as quickly as possible and determine the best scheduling of each sample to provide a consistent minimal turnaround time and maximum throughput of the analytical processes. The steps and organization of those steps in the process are designed to avoid accumulation of specimen containers at the input to the system or at other stations of the system. Modules of the laboratory system can operate at a throughput speed that allows processing of samples at the maximum throughput of the upstream processes. However, in some embodiments, at the aliquoter unit, the throughput may be managed by the introduction of samples upstream and by small queues at each aliquoting station.

Figure 2:
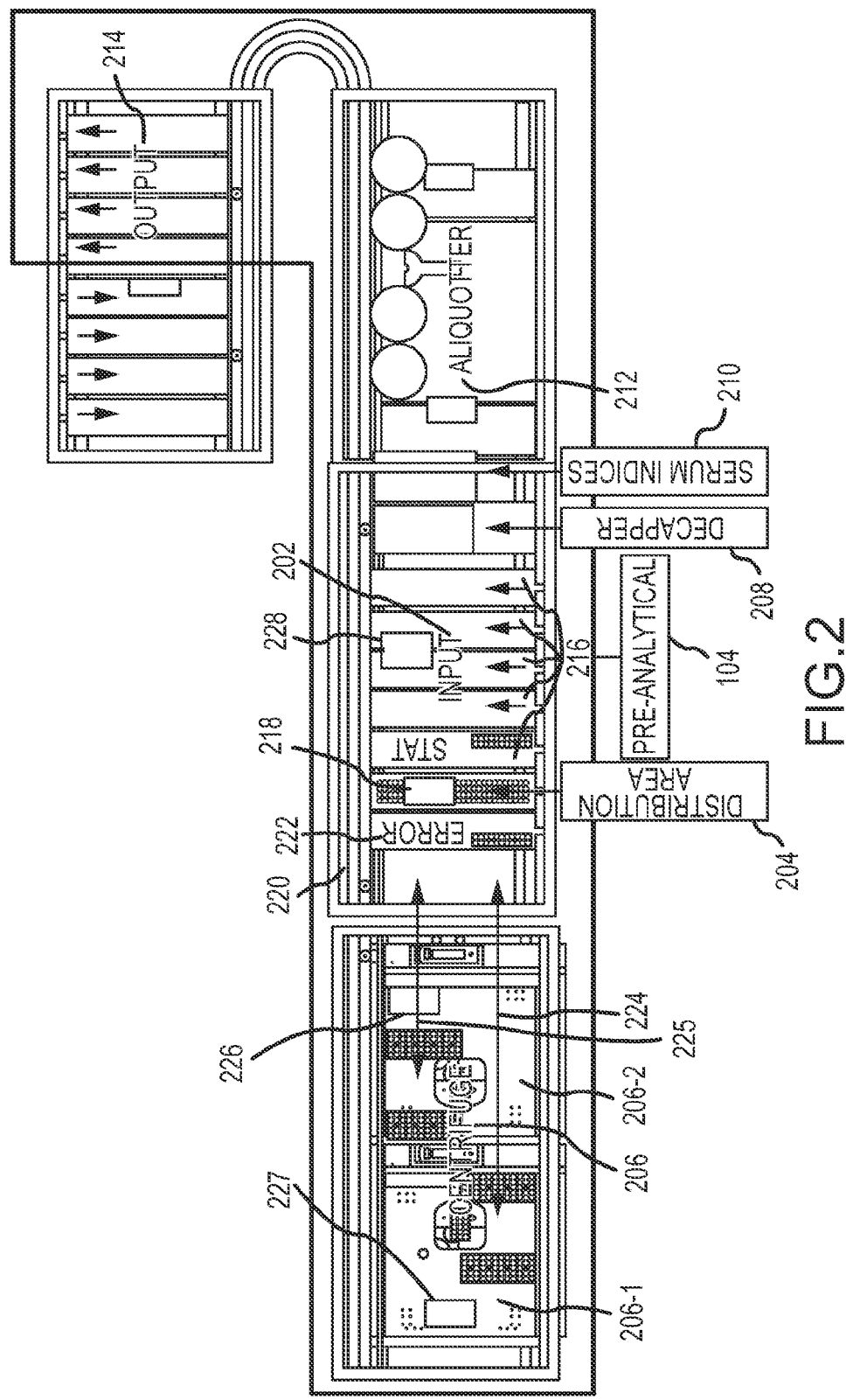
FIG. 2 depicts a block diagram of components associated with a pre-analytical phase of a laboratory automation system.

FIG. 2 is a more detailed depiction of the components associated with the pre-analytical phase 104. The components associated with the pre-analytical phase 104 can include modules such as input module 202, distribution area 204, centrifuge 206, decapper 208, serum indices measurement device 210, aliquoter 212, and output/sorter 214.

Input Module

The input module 202 shown in FIG. 2 is the point at which a specimen container is introduced to the laboratory system. Racks of tubes and/or individual tubes can be loaded onto one of several lanes 216, which may be manually operated drawers and/or automated devices. In FIG. 2, five lanes 216 are depicted. However, the lab system can have any number of lanes 216. The lanes 216 can be prioritized according to automated or user-established scheduling. In some embodiments, the highest priority lane (short turnaround time or "STAT") may have a fixed position for accepting a group of individual tubes from the user. Once tubes are loaded in the STAT lane, they become the next tubes processed. Other lanes can be assigned different priority levels in any manner. For example, when the drawers are manually operated, assigning one priority to at least two of the drawers and another priority to at least two other drawers may allow the system to operate continuously on one drawer while the other drawer of the same priority is available to the user.

In some embodiments, while the input module 202 is processing a drawer of samples, the user may be informed that the drawer should not be opened. For example an indicator such as a light on the drawer or a lock on the drawer may be used to warn the user. This may help maintain the process integrity and maximize throughput. When processing of the contents of the first drawer is complete, the drawer may be identified to the user as available, and the system may automatically begin processing another drawer. Additionally, the samples can be transferred to and from the drawers 216 of the input module 202 using an input module gripper 228.

In some embodiments of the invention, a "region" concept can be used. A "region" can be the basic abstraction for the usage of drawers, rack holders, trays and racks. For example, a region can be a set of tube positions within a rack in one embodiment of the invention. A region can be assigned either tube characteristics (e.g., STAT, sample type, pre-spun, cap type) or a single processing instruction. In embodiments of the invention, a tube characteristic or instruction can be assigned to one or more regions, which allows for a more robust routing scheme.

Distribution Area Module

Referring again to FIG. 2, from the lanes 216 within the input module 202, one or more distribution area grippers 218 may select the highest priority tube and transport it to a fixed matrix called the distribution area 204. The distribution area 204 is capable of distributing a sample container to a designated station of the laboratory automation system. As the input module gripper 228 transfers a specimen to distribution area 204, the gripper 228 can gather information about the specimen. For example, one or more liquid levels of fluid within the specimen container may be measured, e.g., by systems associated with gripper 228. In some embodiments, the sample tube may be photographed, e.g., by systems associated with gripper 228. The information gathered in this manner can be analyzed to determine the tube's manufacturer, diameter, height, cap color, etc. Volumes of the sample's components can be calculated, and an estimate of the total tube weight can be made. This weight can be later used to aid in balancing the centrifuge adapters in the centrifuge module 206, as will be discussed in more detail below.

To protect the distribution area 204 from becoming filled with low priority tubes, a limit can be set on the number of tubes loaded into this area from the low priority input lanes. Moreover, the distribution area 204 may have a reserved area to ensure STAT samples have continuous access to the distribution area 204 from the STAT drawer in the input module 202.

The distribution area 204 can be the holding area which permits the system to access test information associated with the sample tube in the association phase 102 and plan the analysis process for the sample. This enables the system to schedule a sample tube's process with respect to the other sample tubes currently on the system. Scheduling enables the efficient processing of samples based upon priority without overloading any step in the overall system, permitting the optimization of turnaround time and throughput. Furthermore, the sample's schedule can be updated throughout the process as the system's activity or availability changes, providing real time active control of the sample.

Once the schedule is planned by the distribution area module 204, a robotic gripper 218 then selects the sample tube that is the next tube to be transferred to the next module based on the priority of the tubes within the distribution area 204. The selected sample tube is transported from the distribution area 204 to the conveyance system 220, to the centrifuge module 206, or to an error area 222 based on the analysis performed by the distribution area module 204.

If the sample tube is being moved to the centrifuge module 206, the tube can be placed into the appropriate centrifuge adapter based upon the earlier weight estimation to ensure proper balance of the centrifuge rotor. In other embodiments, the tube can be placed into a centrifuge adapter based on its priority. The centrifuge adapter is the component which carries the tubes upon a shuttle from the distribution area 204 to the centrifuge whereupon a robotic gripper transfers the centrifuge adapter with the tubes to a bucket of the centrifuge.

If the distribution area module 204 determines that the sample tube does not require centrifugation the distribution area robot gripper 218 places the sample into a carrier on the conveyance system 220 with the barcode label properly aligned to the carrier at the direction of the scheduler so as not to overload downstream processes Centrifuge Module The sample tube may be moved from the distribution area 204 of FIG. 2 to the centrifuge module 206 when the distribution area module 204 determines that the sample requires centrifugation before analysis of the sample. Centrifuge module 206 may include one or more automated centrifuges (e.g., centrifuge 206-1 and centrifuge 206-2) and an adapter shuttle for each centrifuge (e.g., adapter shuttle 224 and adapter shuttle 225). Centrifuge module 206 may further include one or more robot grippers (e.g., robot gripper 226 and robot gripper 227). In some embodiments, a robot gripper 226 may be a centrifuge tube gripper used to remove centrifuged sample tubes from adapters 224, 225 and transport the sample tubes to conveyance system 220. A robot gripper 227 may be a centrifuge adapter gripper used to swap adapters into and out of centrifuges 206-1, 206-2.

When a sample tube is to be transported from the distribution area 204 to the centrifuge module 206, the sample tube can be loaded by the distribution area robot gripper 218 into a centrifuge adapter from the distribution area 204. The adapters may accommodate multiple tube sizes for centrifugation. The adapter may be seated on an adapter shuttle 224, 225 that moves between the distribution area 204 and the centrifuge module 206.

Figure 3:
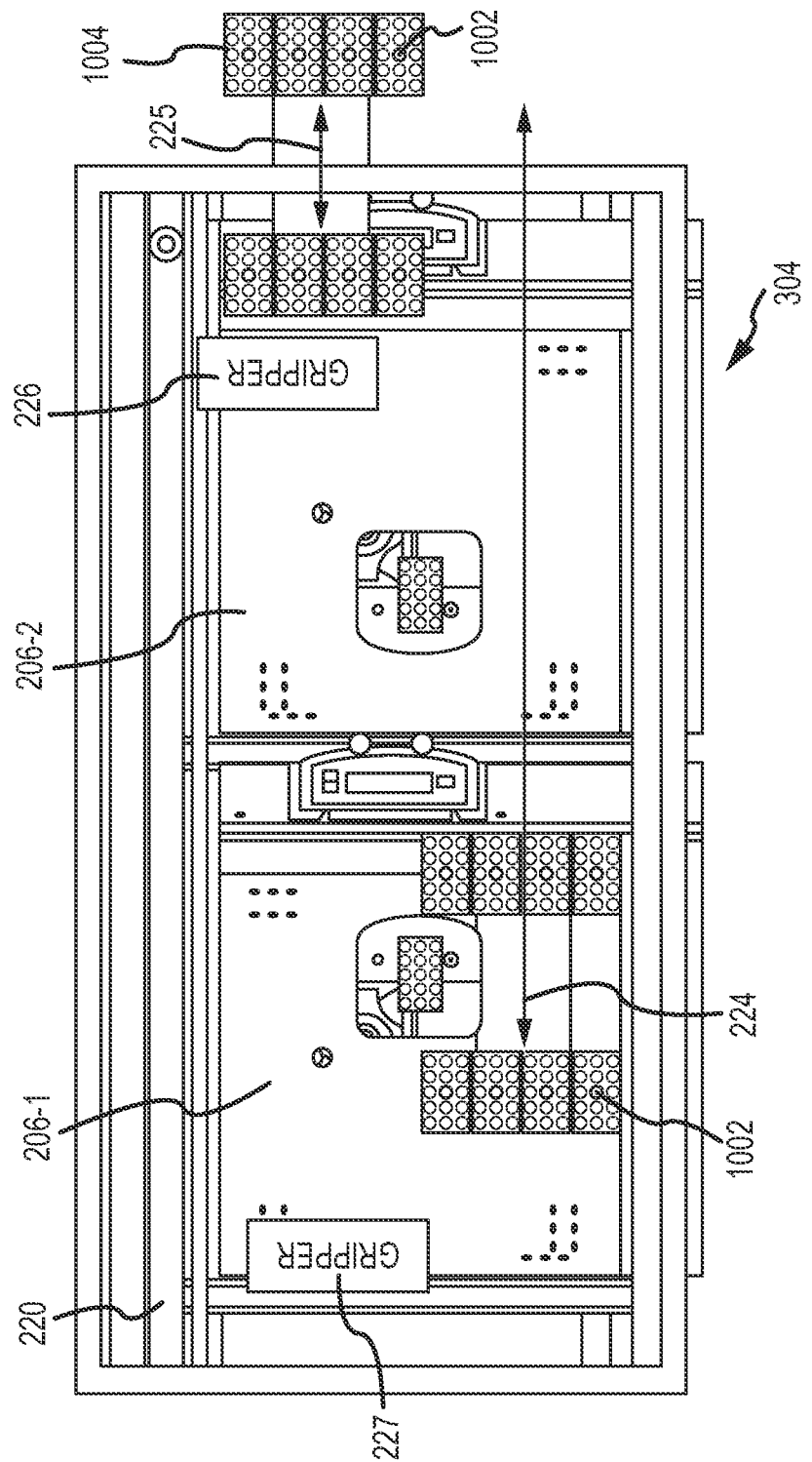
FIG. 3 depicts a block diagram of components associated with a double centrifugation unit.

FIG. 3 depicts a closer view of a double centrifuge unit 304, which was described in detail with reference to FIG. 2. The centrifuge unit 304 can include two single centrifuges 206-1 and 206-2, adapter shuttle 224, and adapter shuttle 225. Each adapter shuttle can hold centrifuge adapters 1002. Centrifuge unit 304 may further include robotic grippers 226, 227.

Figure 4:
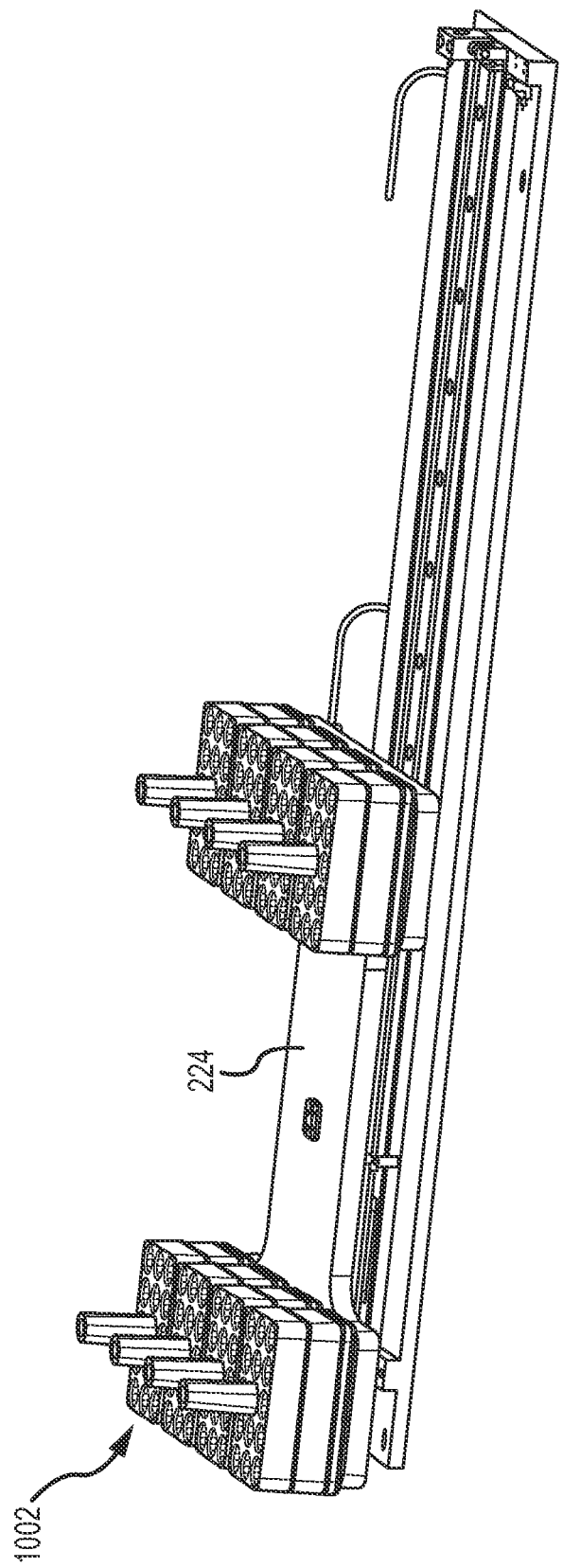
FIG. 4 shows an illustrative shuttle used for transporting centrifuge adapters.

FIG. 4 shows an illustrative shuttle 224 used for transporting centrifuge adapters 1002.

Figure 5:
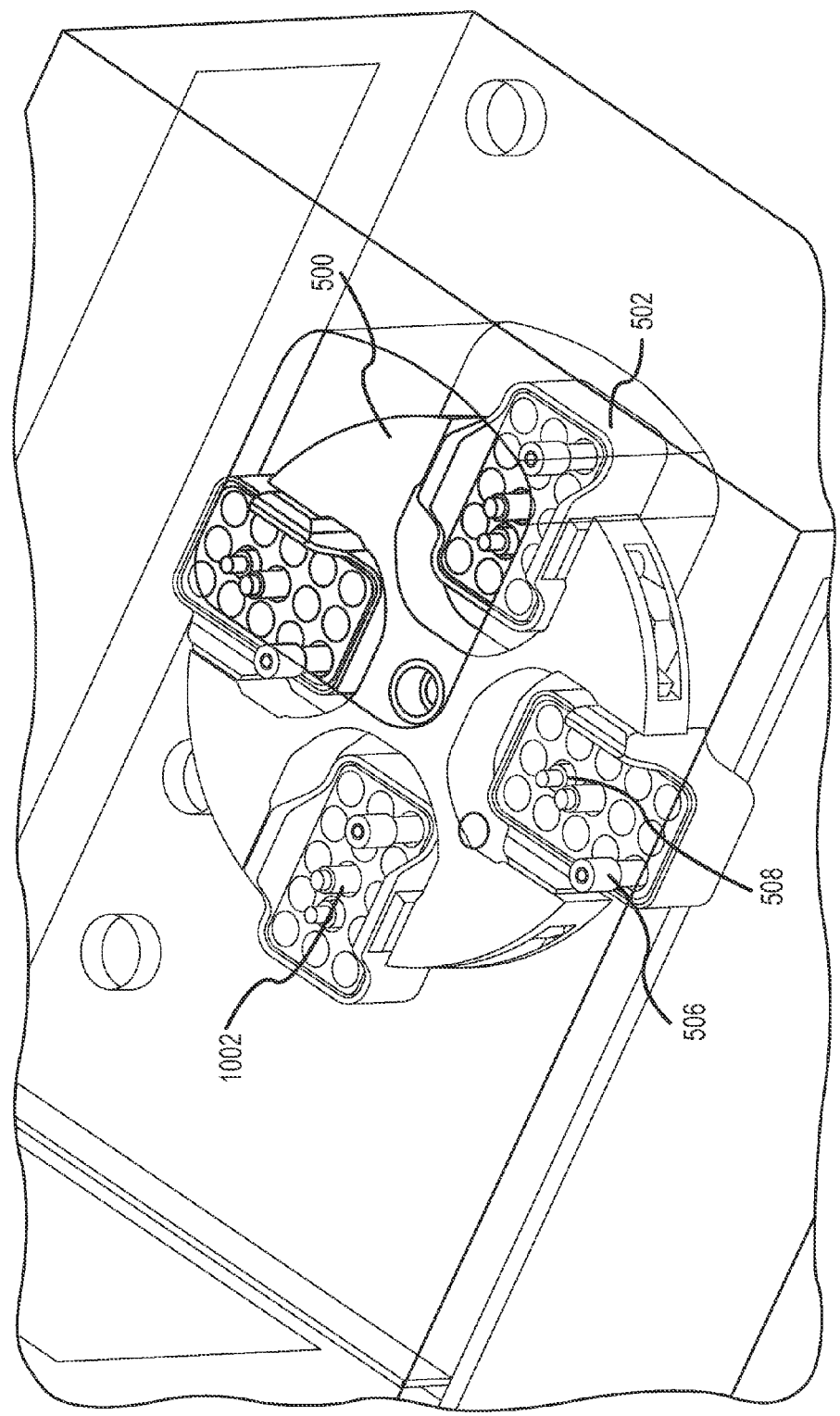
FIG. 5 depicts a centrifuge rotor.

FIG. 5 shows an illustrative centrifuge rotor 500 configured to receive four centrifuge adapters 1002. Centrifuge adapters 1002 may be loaded into centrifuge buckets 502 of the centrifuge. Centrifuge adapters are configured to receive one or more sample tubes 506. The centrifuge adapters may be configured to receive different shapes and sizes of sample tubes, as illustrated by the larger sample tube 506 and the smaller sample tube 508 in adapter 1002.

When adapters 1002 loaded with sample tubes arrive at the centrifuge module 206 from the distribution area 204 via the adapter shuttles 224, 225, the adapters 1002 are loaded into an available centrifuge bucket 502. In a preferred embodiment, each centrifuge can accept multiple adapters 1002, e.g., four adapters. In some embodiments, each adapter 1002 can hold a plurality of sample tubes, such as 14 sample tubes.

Of the adapters associated with centrifuges 206-1, 206-2, a subset of the associated adapters (e.g., two adapters) may reside on each adapter shuttle. In some embodiments, the following processes may occur simultaneously: distribution area gripper 218 loads tubes into an adapter, centrifuge tube gripper 226 unloads tubes from another adapter on an adapter shuttle and moves the unloaded sample tubes to sample carriers on conveyance system 220, centrifuge adapter gripper 227 swaps adapters for a centrifuge (e.g., 206-1), and a another centrifuge (e.g., 206-2) spins an adapter set. An adapter shuttle may transfer adapters to a centrifuge when one or more of the following occurs: a centrifuge is available, an adapter filling time is expired (which may depend on the scheduled starting time for a centrifuge), or adapters for unloading are empty.

The configuration of the adapters allows for simplified delivery of sample containers to and removal of sample containers from the centrifugation buckets. Once loaded into a centrifuge bucket, the adapters can be centrifuged.

Once centrifugation is complete, centrifuge adapter gripper 227 can remove the adapters from the centrifugation bucket. The adapter shuttle can then move back to the tube loading/unloading position. With the adapter shuttle at the loading/unloading position, centrifuge tube gripper 226 may remove sample tubes from the adapters and place the tubes in carriers on the conveyance system 220 for transport to the next module. Sample tubes may be removed from adapters and placed in a temporary buffer. For example, when a downstream module is temporarily non-operational or otherwise unavailable, the sample tubes may remain in the temporary buffer. When the downstream module becomes available, the sample may be removed from the buffer and placed on conveyance system 220. If the downstream module will be unavailable for an extended period of time, the sample can be placed on conveyance system 220 to be transported to error area 222.

The timing for loading tubes into an adapter at the distribution module 204, sending the tubes in the adapter to the centrifuge module 206 via the adapter shuttle 224, loading the adapter into a centrifuge bucket, centrifuging the samples, unloading the adapter from the centrifuge bucket, and unloading the tubes from the adapter can be established such that the process is continuous, allowing for the continual centrifugation of samples as they arrive at the centrifuge module 206 from the distribution area 204. As the centrifuge completes a spin cycle, the last tube in the distribution area 204 can be loaded by the distribution area gripper 218 into an adapter, and the shuttle 224 can move the adapter to a centrifuge in the centrifuge module 206. At the same time, an automated door on the centrifuge opens and provides access to a bucket as the rotor indexes into position at the doorway.

In one embodiment, a centrifuge adapter gripper 227 in the centrifuge module 206 can remove an empty adapter from the adapter shuttle and place the empty adapter on a deck of centrifuge module 206. Subsequently, the centrifuge adapter gripper 227 can remove an adapter that is in a centrifuge bucket. The centrifuge adapter gripper 227 can move the adapter that was removed from the centrifuge bucket to the area of adapter shuttle from which the empty adapter was removed. Next, the centrifuge adapter gripper 227 selects an adapter that has been recently loaded with tubes from the distribution area 204 and deposits it into the empty bucket. While the centrifuge rotor indexes to the next bucket, a previously emptied adapter is moved to the open position on the shuttle 224 for loading with tubes from the distribution area 204 when the shuttle 224 returns to the distribution area 204.

After the final adapter is loaded into the centrifuge, the centrifuge door, which may be an automated door may be closed to allow the centrifuge cycle to begin. The empty adapter that was on the centrifuge module deck can be placed on the adapter shuttle. The adapter shuttle may move back to the distribution area 204, and a centrifuge tube gripper 226 begins to unload tubes from the adapters removed from the buckets into carriers on the conveyance system 220. As the tubes are moved from the adapter to the carrier, liquid level detection can be performed with centrifuge tube gripper 226. For example, a liquid level measurement can be performed as described in more detail below. In some embodiments, the heights of the sedimentation layers are measured and the barcode on the sample container is read and/or aligned for the carrier. If insufficient serum or plasma is present in a centrifuged sample container, the sample container may be sent to an error area located in the output module 214.

In an alternative embodiment, a shuttle can have additional space for one or more adapters. For example, the shuttle can have a number of positions for adapters that exceeds the numbers of adapters in an adapter set by one. The additional space may be located on the loading side of the shuttle. Rather than moving an empty adapter to a temporary location such as a centrifuge module deck, as described above, the adapter may be placed at the additional space on the shuttle.

If the scheduling algorithm predicts the overloading of an analyzer with samples from the centrifuge module 206, the centrifuge module gripper 226 can unload the samples and distribute the samples from the adapters to the conveyance system. In some embodiments, the full cycle time of the centrifuges can be greater than or equal to, e.g., 360 seconds. In order to ensure optimal turn-around time and throughput the centrifuges are kept, e.g., 180 seconds out of phase for a 360 seconds centrifugation cycle. In some embodiments, downstream processes do not prevent the unloading of samples from the centrifuge adapters. If all the remaining samples in an adapter are destined for unavailable process (es) and depending upon the unavailable process, sample tubes can either be moved to a buffer in the centrifuge instrument or moved to another buffer area elsewhere in the system.

The centrifuge module 206 may include an automated centrifuge controlled by a centrifuge controller. The automated centrifuge can be loaded with multiple centrifuge adapters or receptacles, each adapter receiving multiple sample tubes. The centrifuge includes a motor coupled to a spindle, a rotor assembly, a controller, a lid, and optionally, a lid drive. The centrifuge controller indexes or stops the spindle at selected positions for automated placement and removal of either tubes, adapters or buckets. The lid has a closed position and an open position, and the lid opens and closes in response to instructions from the centrifuge controller.

Various techniques may be used to balance the weight distribution among adapters that are to be loaded into a centrifuge. In some embodiments, the weight of a tube may be determined based on information stored in a database of tube weights. The weight of sample material contained in a tube may be determined based on a measured liquid level or liquid levels in a sample tube and a known density of the liquid or liquids. In another embodiment, sample tubes may be weighed by input module gripper 228 prior to being loaded into centrifuge adapters.

In another embodiment, specimen weights can be determined by one or more balances, for example, a balance located in the distribution area or a balance of a conveyor track. The balance can measure the combined weight of the sample tube and the sample contained in the tube. This may occur as the sample tubes are carried by a conveyor track. To obtain a weight of the sample, a known weight of the sample tube can be subtracted from the combined weight. The known weight can be stored in a database of known tube weights. The sample weight may be determined using a central controller associated with the laboratory system or by another controller of the system. The controller may be communicatively coupled to the database.

Alternatively, centrifuge module 206 may comprise a scale having sites for receiving and holding a plurality of adapters, and a balance controller for selectively depositing sample tubes in cavities of the adapters while correlating incremental weight changes with the locations of each deposit for equalizing weight in pairs of the adapters.

The balance controller can be implemented as a balance program within the central controller. The balance program maintains a database of sample container weights. When a container's weight is combined with the sample's weight, the balance program can determine the optimum adapter cavity in which to place it thereby maintaining a balanced rotor within a tolerance. Sample weights are the product of density estimates and the sample volumes calculated from liquid level measurements and container geometry obtained during the initial pick-up from the input. In some embodiments, balance system may also include a supply of dummy loads in buckets for limiting weight variations between buckets. The dummy loads may be weighted for limiting the weight variations to not greater than, e.g., 10 grams between members of each pair of buckets.

The centrifuge controller may operate to perform a number of functions, such as receiving and storing centrifuge spin profiles including a rotor spindle speed and duration; indexing the rotor's sample stations into an access position, spinning the rotor in accordance with the cycle profile, stopping the rotor with a predetermined sample station at the access position, etc.

If two or more centrifuges are used in the pre-analytical system, the centrifuges may be synchronized and/or kept out of phase. For example, the starting time of a spinning cycle for centrifuge 206-1 may be scheduled at a different time from a spinning cycle for centrifuge 206-2. Because centrifuges 206-1 and 206-2 do not start spinning at the same time, high priority sample tubes may be processed quickly. In some embodiments, spin cycles for the centrifuges are scheduled such that at least one centrifuge is available to process a high priority sample tube at any time.

In an exemplary embodiment, the centrifuges may be run synchronized and out of phase on a fixed timetable such that a centrifuge is available at predetermined intervals. For example, a centrifuge cycle may have a six minute duration, which can include the time required to swap adapters out of and into the centrifuge. In a system with two centrifuges, the centrifuge cycles may be out of phase such that one of the centrifuges is available every three minutes. (e.g., one of two centrifuges is available every three minutes).

Centrifuge Workflow

Figure 6:
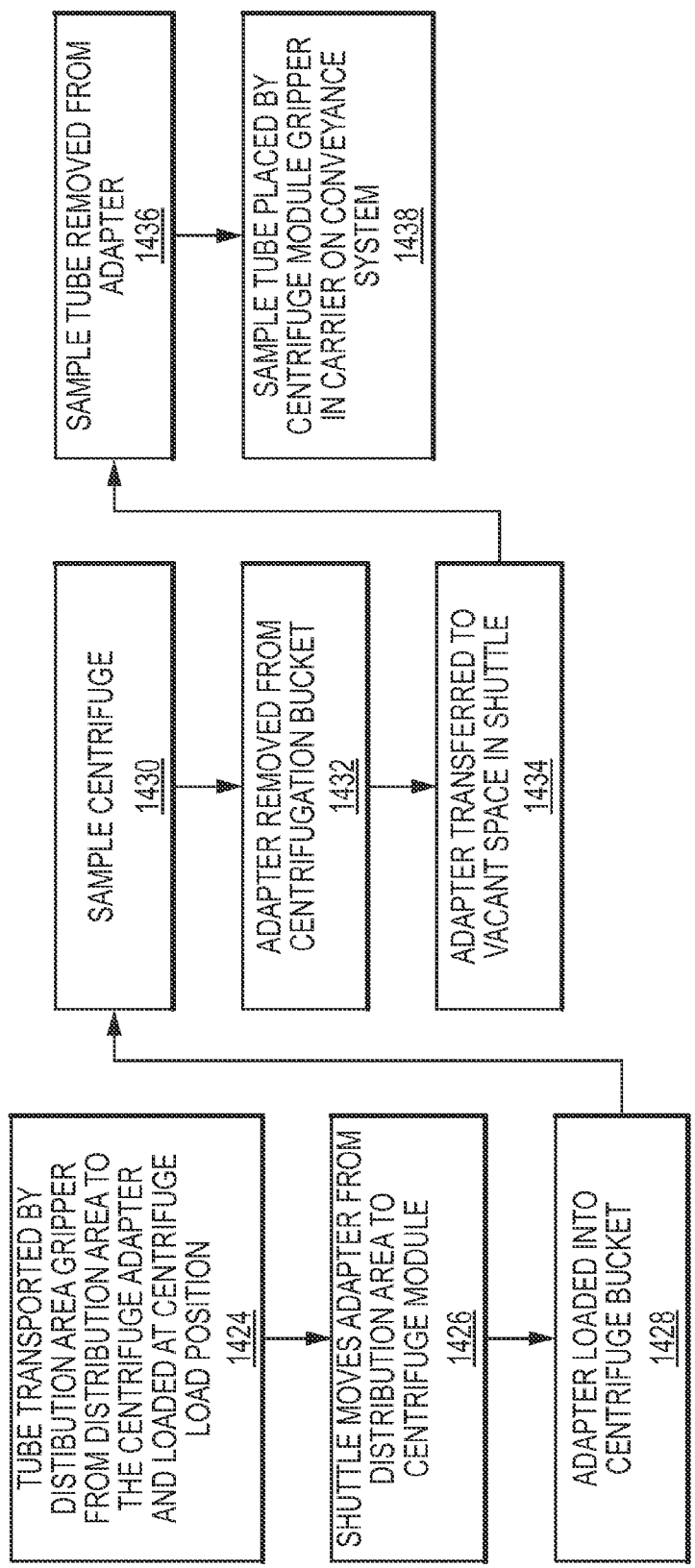
FIG. 6 is a flow chart showing an illustrative example of the centrifuge system workflow.

FIG. 6 is a flow chart showing an illustrative example of the centrifuge system workflow. When the scheduler selects a sample container for centrifugation, the tube may be loaded by the distribution area gripper 218 into the appropriate centrifuge adapter 1002 at the centrifuge load position 1004 to ensure a balanced centrifuge rotor. At operation 1424, when the sample container 506 is selected for centrifugation, the sample container 506 is transported by distribution area gripper 218 from distribution area 204 to the centrifuge adapter 1002.

As the centrifuge cycle is ending for adapters already loaded into the centrifuge 206-1 or 206-2, the newly loaded centrifuge adapters 1002 are moved to the appropriate centrifuge 206-1 or 206-2. The adapters sit on an adapter shuttle (e.g., 224 or 225) that moves from centrifuge load position 1004, between the manager unit 700 and the centrifuge unit 304, to the appropriate centrifuge 206-1 or 206-2, as indicated at operation 1426. The adapter may be loaded by a robot gripper, such as centrifuge adapter gripper 227, into a centrifuge bucket 502, as indicated at operation 1428. The sample may be centrifuged, as indicated at operation 1430. A previously emptied adapter may be moved from a shuttle (e.g., 224, 225) to a temporary location to create a vacant space in the shuttle. The temporary location may be, e.g., a temporary holding area of a centrifuge area or a dedicated buffer region. The adapter may be removed from the centrifuge (e.g., removed from a centrifugation bucket), as indicated at operation 1432, and transferred to the vacant space in the shuttle, as indicated at operation 1434. When all adapters have been swapped and the shuttle is moved to the unload position, a sample tube may be removed from the centrifuge adapter 1002 by a robot gripper, such as centrifuge tube gripper 226, as indicated at operation 1436. The sample tube may be placed by centrifuge tube gripper 226 into a carrier on conveyance system 220, as indicated at operation 1438.

Centrifuge adapters 1002 that are loaded with sample tubes may be swapped with the adapters in the centrifuge unit 206-1 or 206-2 by centrifuge adapter gripper 227. The centrifuged adapters can then be removed from the centrifuge unit 206-1 or 206-2 and placed in a vacant space in the shuttle as indicated at 1432. For example, the centrifuged adapters may be placed in specific spots on the shuttle so that when the shuttle returns to the manager unit 700, the tubes can be unloaded by centrifuge tube gripper 226 from the adapters and placed onto the conveyance system 220. The newly loaded adapters 1002 from the manager unit 700 are placed inside the centrifuge 206-1 or 206-2. After the centrifuge adapter has been loaded into the centrifuge rotor, the centrifuge rotor may index to allow loading of a subsequent uncentrifuged centrifuge adapter. An adapter which was previously emptied of its sample tubes may be moved by the centrifuge adapter gripper 227 from an unloading spot on the shuttle to a vacant spot on the shuttle. For example, for a shuttle such as the illustrative shuttle of FIG. 11(b), a first end of the shuttle 230 may be an unloading spot and a second end 232 of the shuttle may be a vacant spot. Moving the adapter to a vacant spot on the shuttle may occur simultaneously with the indexing of the centrifuge rotor. The empty adapters can then be loaded with new sample tubes in the manager unit 700. The swapping of adapters may continue until all adapters of a centrifuge rotor have been exchanged, allowing the adapter that was placed in a temporary location to be moved to the last empty spot in the shuttle for emptied adapters. Illustrative centrifuge adapter swapping sequences are described further with reference to FIG. 7.

The shuttle may return to its home position where adapters can be loaded with sample tubes by distribution gripper 218 and/or unloaded by centrifuge tube gripper 226. When samples are unloaded from the adapters and transferred to a carrier on the transport by the centrifuge tube gripper, a barcode label on the sample tube may be aligned to the carrier and a liquid level measurement may be made to ensure that the tests required for the sample can be completed. Thus, the centrifuge tube gripper 226 may have a liquid level detection functionality as described with reference to input module gripper 228. If insufficient sample material is present for further processing of the sample, the tube can be processed according to procedures established for insufficient sample material conditions. For example, the sample tube may be processed according to predefined rules which dictate the tests to complete or the sample may be sent to a Sample in Question (SIQ) rack in output module 214.

While adapters are being swapped in the centrifuge unit 304, the scheduler may direct tubes that do not require centrifugation to be moved by the distribution area gripper 218 from the distribution area 204 to the conveyance system 220, bypassing the centrifugation unit 304, as indicated at operation 1440.

Centrifuge Adapter Swap Sequence

Figure 7:
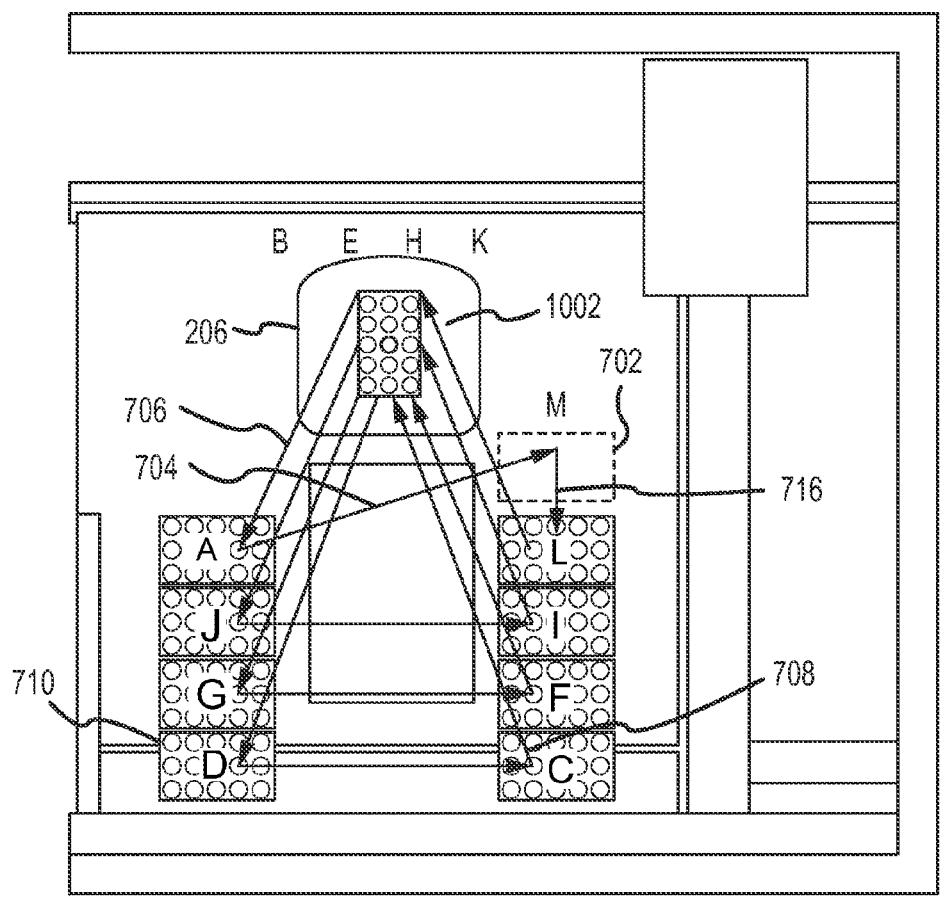
FIG. 7 depicts an illustrative adapter swap sequence for a centrifuge.

FIG. 7 depicts an illustrative adapter swap sequence for a centrifuge according to a first embodiment. Although a single centrifuge adapter 1002 is shown in centrifuge 206, positions B, E, H and K of centrifuge 206 correspond to four centrifuge buckets that can receive centrifuge adapters 1002. A centrifuge with four centrifuge buckets is shown in FIG. 5. A previously unloaded centrifuge adapter (e.g., centrifuge adapter 1002) is moved by centrifuge adapter gripper 227 from shuttle position A to temporary holding area M (702), as shown at 704. An unloaded centrifuge adapter is a centrifuge adapter from which all sample tubes have been removed. Next, a previously centrifuged ("spun") centrifuge adapter is moved by centrifuge adapter gripper 227 from area B of centrifuge 206 to the vacant space on shuttle position A, as indicated at operation 706. Shuttle positions A, J, G, and D can be collectively referred to as first shuttle position 710. At operation 706, the centrifuge adapter 1002 is removed from a centrifuge bucket 502 of centrifuge 206. An adapter 1002 loaded with samples that have not been centrifuged is then moved by centrifuge adapter gripper 227 from shuttle position C to the area B of the centrifuge, as indicated at operation 708. Shuttle positions L, I, F and C can be collectively referred to as second shuttle position 712.

Subsequently, a previously emptied centrifuge adapter is moved by centrifuge adapter gripper 227 from shuttle position D to shuttle position C. A previously spun centrifuge adapter is moved by centrifuge adapter gripper 227 from area E of centrifuge 206 to the vacant space on shuttle position D. An adapter loaded with samples that have not been centrifuged is moved by centrifuge adapter gripper 227 from shuttle F to area E of the centrifuge 206.

The sequence continues with a previously emptied centrifuge adapter moved by centrifuge adapter gripper 227 from shuttle position G to shuttle position F. A previously spun centrifuge adapter is moved by centrifuge adapter gripper 227 from area H of centrifuge 206 to the vacant space on shuttle position G. An adapter loaded with samples that have not been centrifuged is moved by centrifuge adapter gripper 227 from shuttle I to the area H of the centrifuge 1680.

Next, a previously emptied centrifuge adapter is moved by centrifuge adapter gripper 227 from shuttle position J to shuttle position I. A previously spun centrifuge adapter is moved by centrifuge adapter gripper 227 from area K of centrifuge 206 to the vacant space on shuttle position J. An adapter loaded with samples that have not been centrifuged is moved by centrifuge adapter gripper 227 from shuttle position L to the area K of the centrifuge 206 indicated at K. The adapter that was moved to temporary holding area M is moved to the vacant space in shuttle position L, as indicated at operation 716.

In this way, spun adapters are swapped out of a centrifuge and unspun adapters are swapped into the centrifuge.

The scheduler determines the order that samples are removed from the adapters and unspun samples are removed from the distribution area. High priority samples (STAT) may be removed first. If a downstream process such as aliquoting in aliquoter unit 212 is unable to handle the flow of samples and the next centrifuge cycle is ready to begin, the samples can be removed from the adapters and placed into a buffer at the back of the centrifuge 206. In some embodiments, the lowest priority samples are removed first to allow more time for the higher priority samples to advance. The scheduler may advance samples from the buffer when downstream processes become available and according to established priorities. If a sample requires another spin cycle, the sample may remain in the adapter to be spun again.

Centrifuge Adapter Loading Sequence

Figure 8:
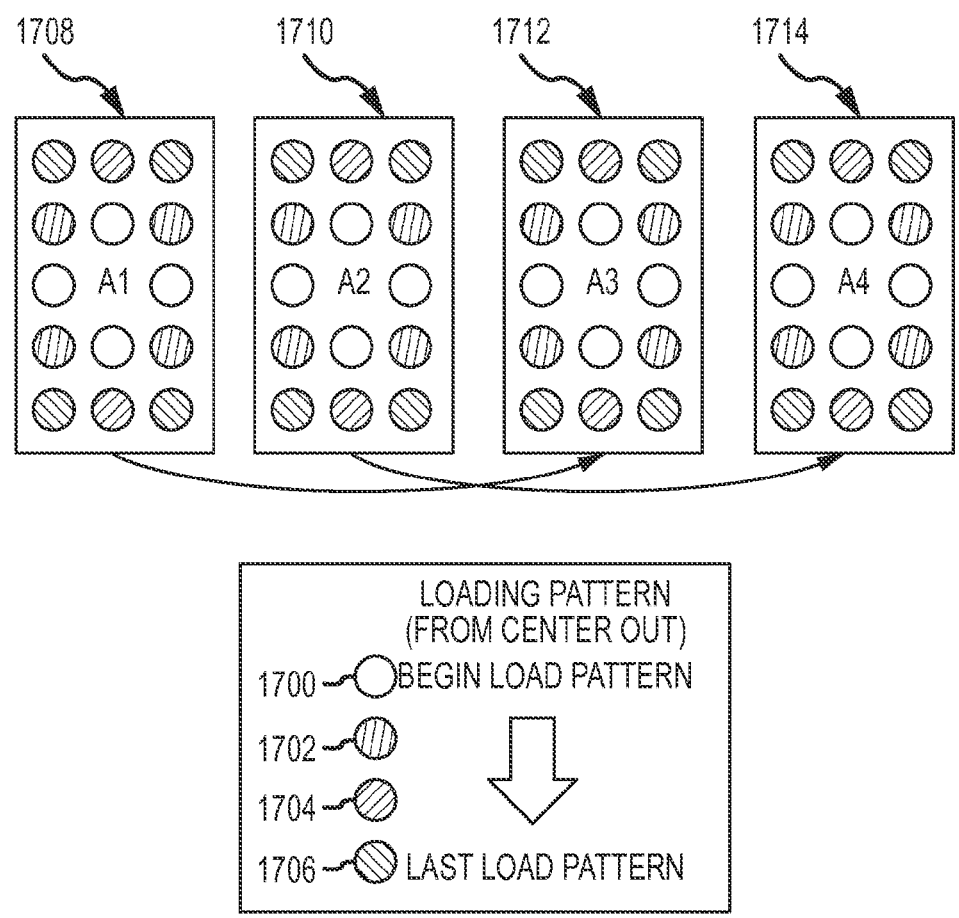
FIG. 8 depicts an illustrative adapter loading sequence for a centrifuge.

FIG. 8 depicts an illustrative adapter loading sequence for a centrifuge. In order to prevent imbalance of the centrifuge rotor, centrifuge adapters 1002 may be loaded in a manner that yields a balanced centrifuge rotor. The weight of each sample tube can be measured and/or estimated from the product of measured sample volume multiplied by a known density for the sample material. In some embodiments, sample tube weights can be determined by one or more balances, for example, a balance located in the distribution area or a balance of a conveyor track that measures sample tube weights as the sample tubes are carried by a conveyor track.

The centrifuge can be loaded according to the following sequence. A first sample tube with a highest centrifugation priority can be identified by the scheduler in the distribution area 204. Adapter A1 (1708) can be loaded with the first sample tube from distribution area 204 in a position closest to the center position of adapter A1 (1708). A second sample tube with comparable weight to the first sample tube can be selected by the scheduler from distribution area 204 and loaded into a position of A3 (1712) that is the same position occupied by the first sample tube in A1 (1708). A sample tube with the second highest centrifugation priority is identified by the scheduler in distribution area 204 to be the third sample tube. The third sample tube is loaded into a position in adapter A2 (1710) that is closest to the center of A2 (1710). A fourth sample tube with comparable weight to the third sample tube can be selected by the scheduler from distribution area 204 and loaded into a position of A4 (1714) that is the same position occupied by the third sample tube in A2 (1710). The process continues with filling open positions in the adapters A1-A4 (1708-1714) with a first sample tube, a second sample tube, a third sample tube and a fourth sample tube, as described above, to fill the positions indicated in green (1700), then the positions indicated in yellow (1702), then the positions indicated in blue (1704), and then the positions indicated in red (1706), until all adapters are filled. In some embodiments, if a centrifuge cycle is nearing completion (e.g., within 30 seconds of completion), the loading of adapters may halt before all adapters are filled and the centrifuge may be loaded with adapters that have not been filled to capacity.

In some embodiments, a sample tube is loaded into an adapter only if its weight is available. The sample tube weight may be determined, for example, based on a liquid level detection performed by input module gripper 228 cross referenced with a table stored in a memory of a laboratory information system (LIS). If the weight of a sample tube is not available, centrifugation may not be performed for the sample tube. For example, the sample tube may be placed in an error rack rather than being loaded into an adapter.

In an alternative embodiment, sample tubes may be loaded into adapters according to priority order. The sample tubes may be loaded according to the order described above with reference to FIG. 8. To avoid imbalance, a lower priority sample tube may be loaded in lieu of a higher priority sample tube if the higher priority tube would cause imbalance. For example, if a first (e.g., highest priority) tube is heavy and the second and third tubes (e.g., next in priority order) equal the weight of the first tube, the second and third tubes may be loaded to oppose the force of the first tube.

In some embodiments, a request for immediate centrifugation may be issued by the scheduler, in which case adapters that are not completely filled may be centrifuged. For example, if a loaded sample tube is a STAT tube or if the adapter filling time for a centrifuge is expired, the adapter may be centrifuged immediately.

Robotic Grippers

As discussed above, a robotic arm can be used to move a sample tube or any other object (e.g. a centrifuge adapter) from many different locations within the laboratory system (e.g., input robot 228, distribution robot 218, centrifuge robot 226, etc.).

Figure 9:
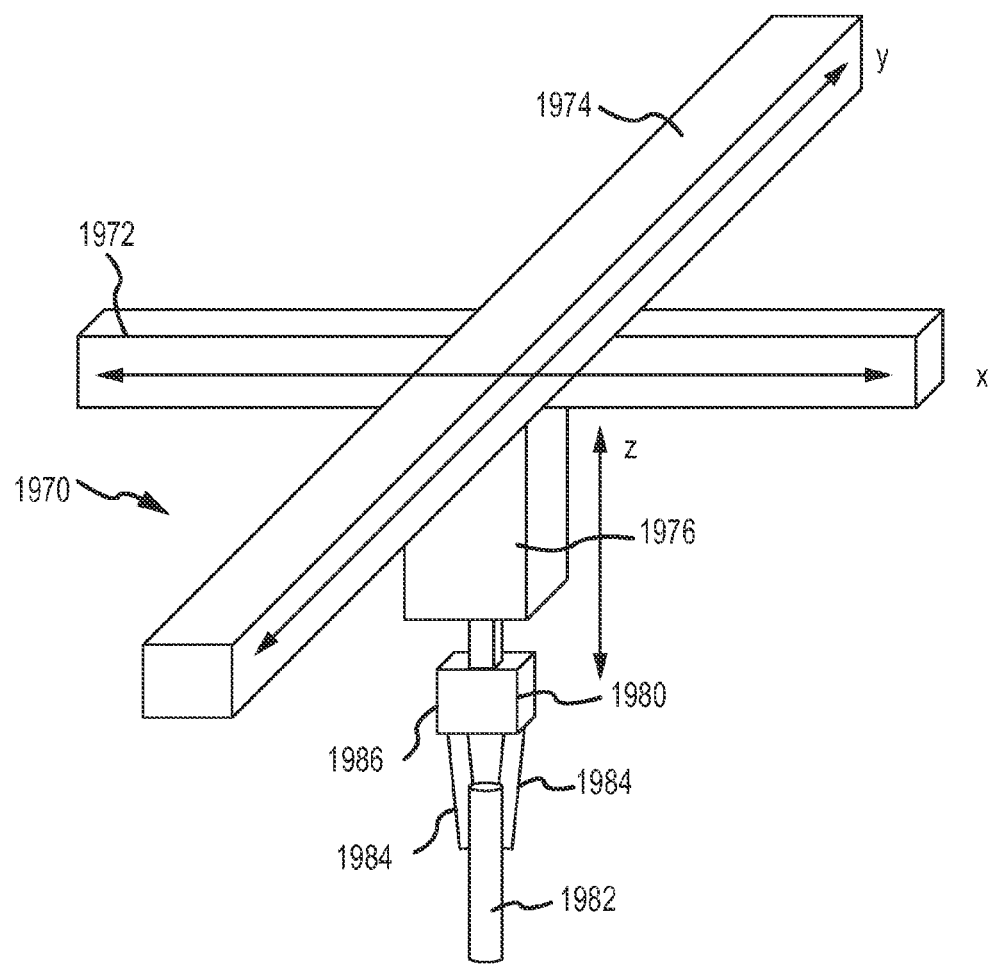
FIG. 9 depicts an example of a Cartesian or gantry robot with three independently moveable directions x-, y-, and z-.

The robotic arm architecture can differ in complexity dependent upon the given task. FIG. 9 depicts an example of a Cartesian or gantry robot 1970 with three independently moveable directions x-, y-, and z-. The x-axis may be defined by an x-axis rail 1972 and the y-axis may be defined by a y-axis rail 1974. The z-axis may be defined by an orientation of a robotic arm 1976 extending in the z-direction. The gantry robot 1970 comprises a robotic arm 1976, and a gripper unit 1980 operatively and physically coupled to the robotic arm 1976. More complex robotic arms may include, for example, the Selective Compliant Assembly Robot Arm (SCARA) or the articulated robotic arm with multiple joint arms. The gripper unit 1980 comprises a gripper housing 1982 and gripper fingers 1984 extending downward from the gripper housing 1986. The gripper fingers 1984 can move inwardly towards each other to grip a sample tube 1982 and outwardly to release a sample tube 1982.

The robotic arm including the gripper unit can be additionally employed for identification and for determination of physical characteristics of the moved object. Therefore, the robotic arm can be equipped with an appropriate identification and determination means (e.g., a camera, a bar code reader, or an absorption and transmission measurement unit). The tube identification, level detection, and tube presence detection units are described in more detail below.

Sample Level Detection

In embodiments of the invention, a camera unit and analysis tool can use the 2-D image captured by the system to determine a sample volume and sample level for the sample in the sample tube.

Figure 10:
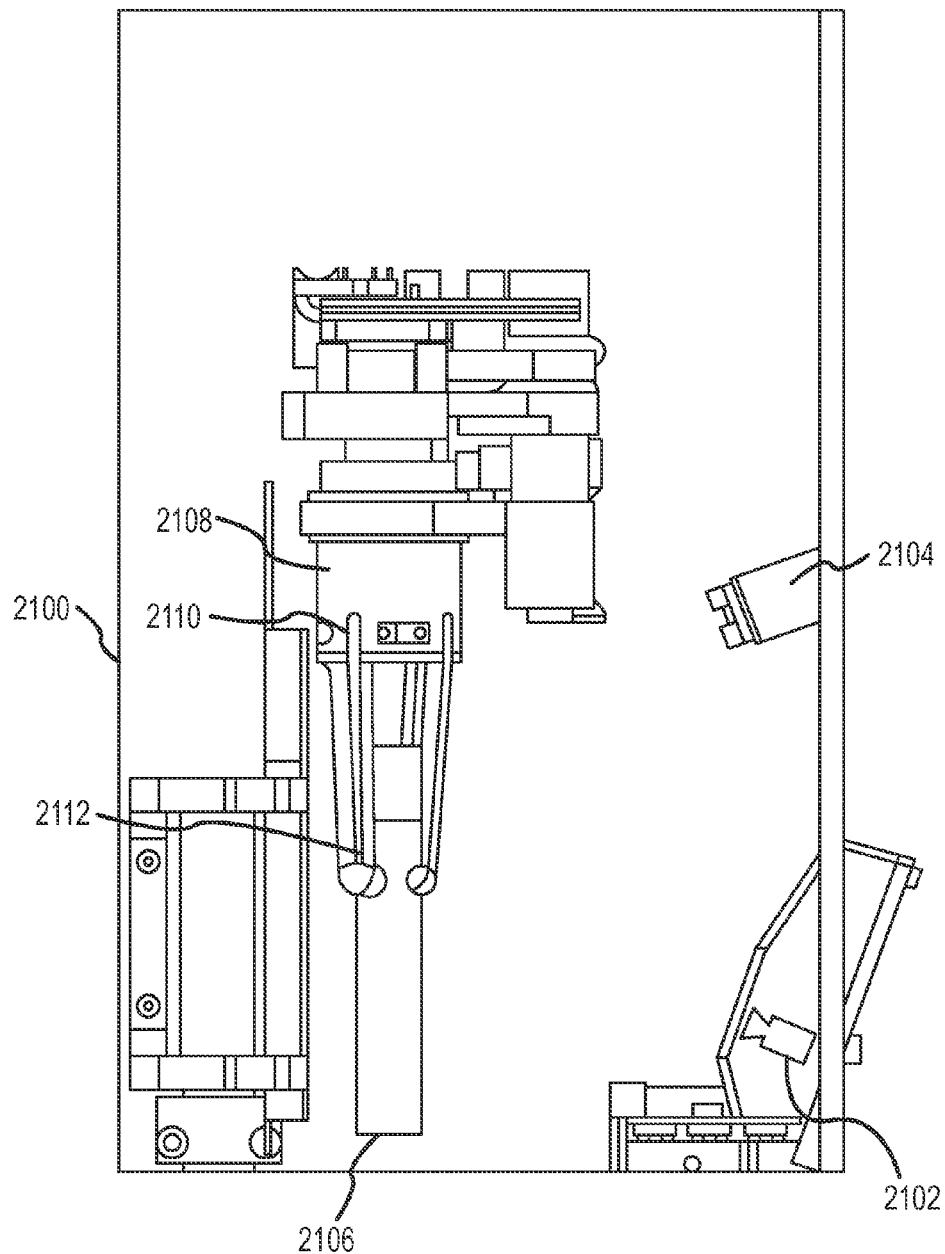
FIG. 10 depicts an exemplary diagram of a camera unit for sample tube detection and analysis.

A sample level detection unit (or assembly) and a sample tube are depicted in FIG. 10. The sample level detection unit includes a chamber 2100. A camera unit 2102 is accommodated in the chamber 2100, which has few and, if possible, no optical reflections. The camera unit 2102 can be aligned with and focused on the sample tube 2106 containing the body fluid. An illumination source 2104 may provide light to the sample tube 2106 so that the camera unit 2102 can take a picture of the sample tube 2106.

The camera unit 2102 can be a still camera, a color image camera, a video camera, a spectral camera or the like. A color image camera, for example a 3CCD video camera, may be used. The settings of the color camera, such as focusing, white balance, diaphragm setting, filling-in, can be permanently preset or adjustable. For example, they can be adjusted with the aid of image evaluation software, as in when the data reported by the image evaluation software to the control software are of reduced quality with reference to store reference data. An algorithm can be used to calculate the sample level and/or volume using known data, such as the type of sample tube used, the type of sample, etc.

As shown in FIG. 10, the camera unit 2102 can be inclined to optimize its view of the sample tube 2106. The sample tube 2106 information can be recorded with comparatively few optical reflections with the aid of this measure.

Arranged above and in the middle relative to the analysis position of the sample tube is a gripper unit 2108 that is controlled by a computer. The gripper unit 2108 grips the sample tube 2106 located in a rack of the input section and lifts it into the analysis position. The gripper unit 2108 can comprise a gripper housing 2110. The gripper unit 2108 can also have a plurality of gripper fingers 2112 which can be used to grip the sample tube 2106.

As an alternative to the liquid level detection device using a camera unit, the liquid level detection may also be accomplished by the use of another type of image acquisition device such as a device that has laser diodes with a defined wavelength and analysis algorithms to evaluate the absorption spectra. A laser diode beam can be focused on sections of the sample tube, and an absorption and transmission measurement of different wavelengths of the focused beam can be measured. The analysis algorithm can then use the measurements to provide the liquid level and volume.

Figure 11:
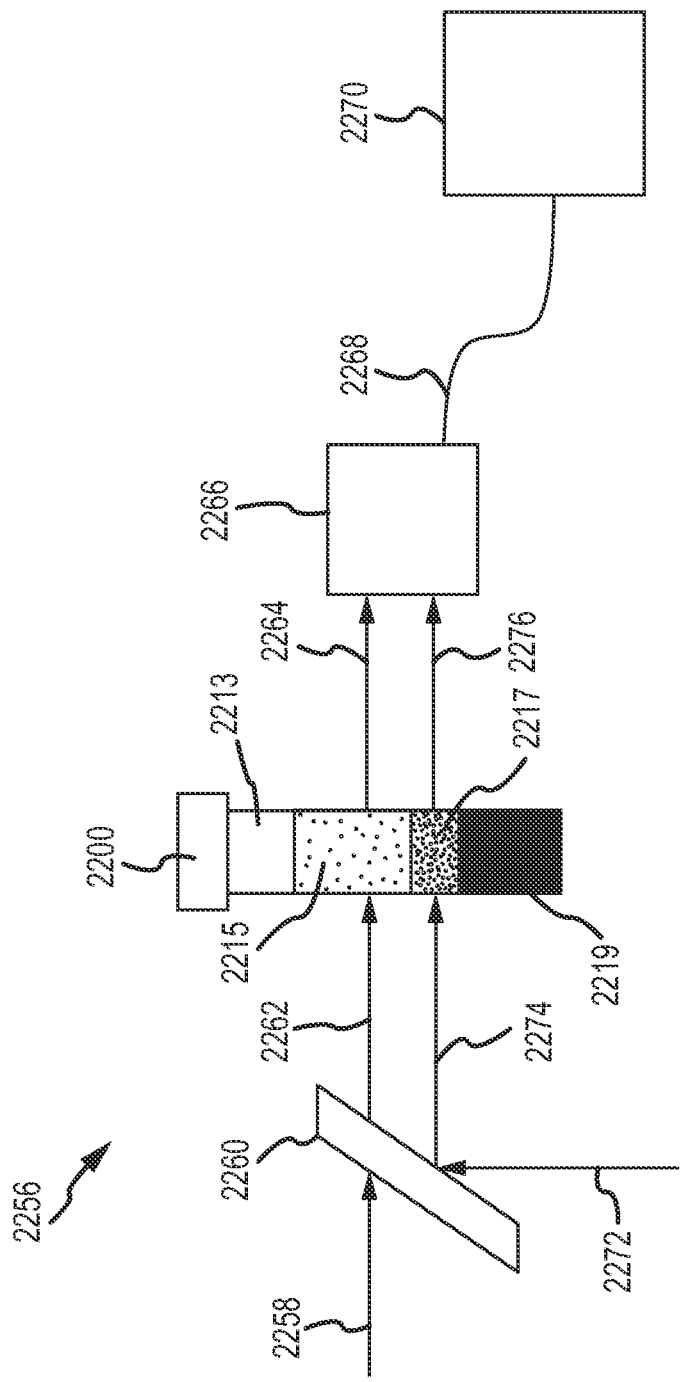
FIG. 11 depicts an example of sample level detection utilizing the analysis of absorption and transmission curves at distinct wavelengths.

FIG. 11 depicts an example of sample level detection utilizing the analysis of absorption and transmission curves at distinct wavelengths. In instances in which blood samples are provided with the sample tube container, the system may additionally be able to detect the distinct levels of serum, plasma, or blood-cake in the total level liquid.

In FIG. 11, a portion of an operable fluid sample interrogation system is depicted generally at 2256. A first source of radiation 2258 (with a second source of radiation 2272 turned off) is arranged to apply a first radiation having a first characteristic wavelength (e.g., 980 nm) to beam combiner 2260, which directs the first emitted radiation 2262 toward a location on the sample tube 2200. The first transmitted radiation 2264 is detected by a detector, such as illustrated photo diode and amplifier arrangement 2266. A signal 2268, corresponding to the intensity of first transmitted radiation 2264 can then be stored and/or manipulated in comparison structure, such as programmable integrated circuit 2270, or a computer. The second source of radiation 2272 (with the first source of radiation 2258 turned off) is arranged to apply a second radiation having a second characteristic wavelength (e.g., 1050 nm) to beam combiner 2260 at a slightly shifted position as the first emitted radiation 2262, which directs the second emitted radiation 2274 parallel to the beam path of first emitted radiation 2262 toward a slightly different location on the sample tube 2200. The second transmitted radiation 2276 is detected by the same detector, such as illustrated photo diode and amplifier arrangement 2266. A signal 2268, corresponding to the intensity of second transmitted radiation 2276 can then be stored and/or manipulated in comparison structure, such as programmable integrated circuit 2270, or a computer.

FIG. 11 further depicts a sample tube that is being measured and analyzed using the wavelength process. As shown, serum 2215 and gel 2217 are mostly transparent to visible light while red blood cells 2219 are substantially opaque. Further, gel 2217 is transparent to infrared light while red blood cells 2219 and serum 2215 are substantially opaque. Accordingly, when the sample tube 2200 has gel 2217 to separate the serum 2215 and red blood cells 2219, it is possible just using infrared light to "see through" different sections. The infrared light reading is strong when the infrared light beam passes through air 2213, drops when the infrared light beam is directed toward the serum, is relatively strong when directed toward the gel 2217, and drops again when directed toward the red blood cells 2219. This analysis performed by the analysis tool allows for the measurement of the sample level/volume of the sample.

The liquid level detection unit can be combined with any of the above-described robotic arms with or without a tube identification unit, and with or without a tube or rack presence detection unit. Further details regarding tube identification units and tube or rack presence detection units can be found in U.S. Provisional Patent Application Nos. 61/556,667, 61/616,994, and 61/680,066.

Centrifuge Drawer

Figure 12:
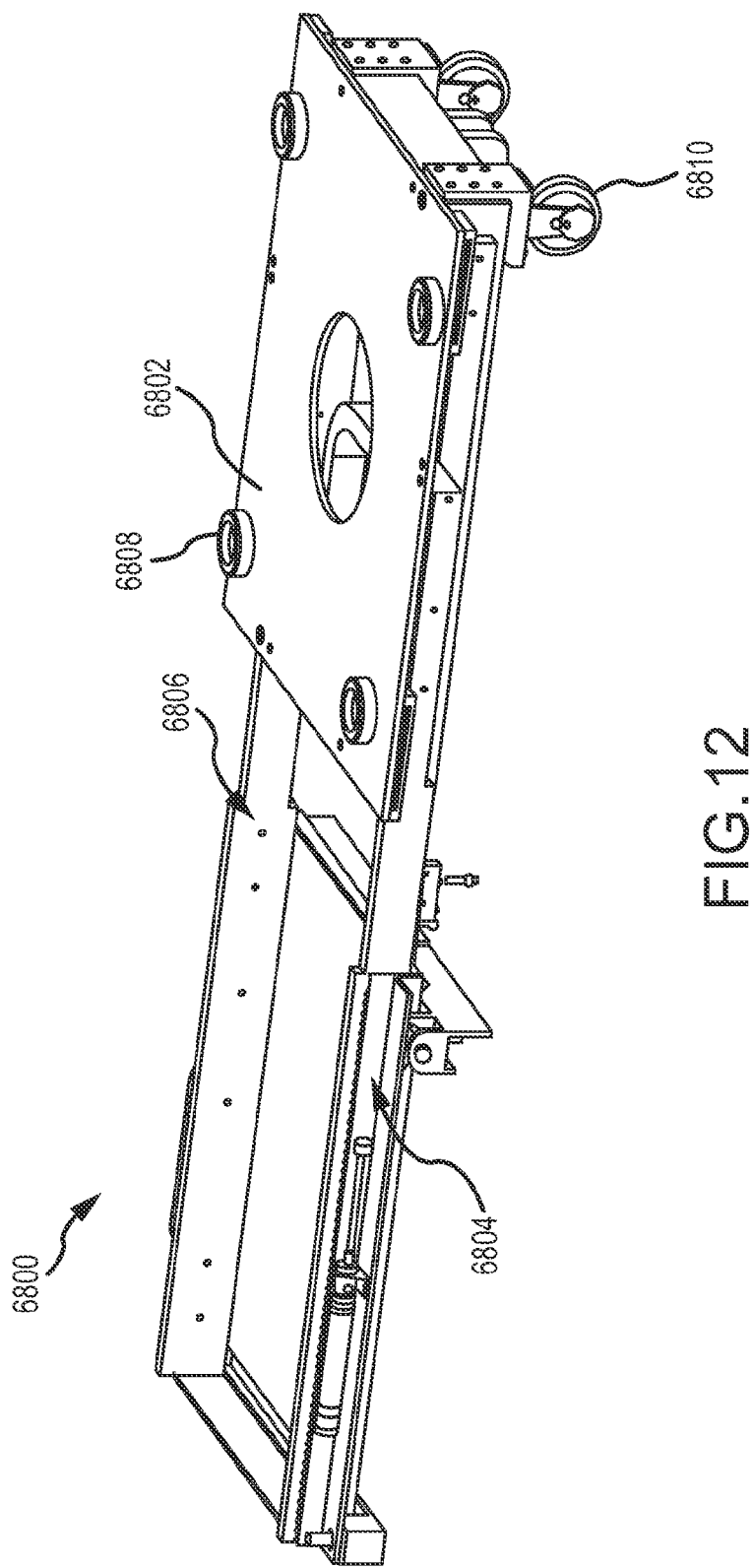
FIG. 12 shows an illustrative centrifuge drawer.
Figure 13:
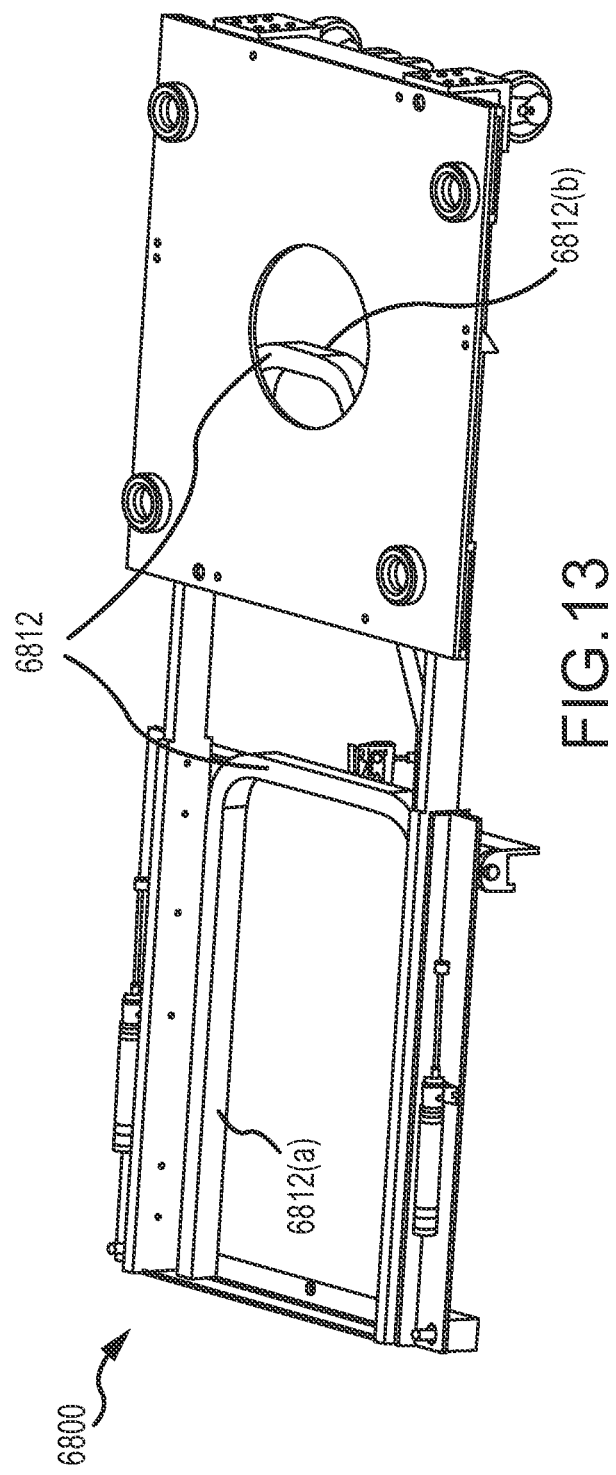
FIG. 13 shows an illustrative cable management device for a centrifuge drawer, according to a first embodiment.

FIGS. 12-19 show various systems associated with a centrifuge drawer 6800. Mounting a centrifuge on a centrifuge drawer can facilitate movement of the centrifuge for service access and can simplify re-installation of a centrifuge. As shown in FIG. 12, centrifuge drawer includes a mounting platform 6802 coupled to frame 6804 via telescoping rails 6806. A centrifuge (not shown) may be mounted on mounting platform 6802. Telescoping rails 6806 can be extended to allow the centrifuge to be withdrawn from its installed position. Telescoping rails 6806 may be locking rails such that the centrifuge can be locked in its installed position (retracted position) or locked in a fully extended position in which the centrifuge is extended away from its installed position. In this manner, the centrifuge is prevented from being moved by the drawer while a centrifuge cycle is in progress. In some embodiments, centrifuge drawer 6800 includes alignment pucks 6808 to mechanically hold the position of the centrifuge to frame 6804. Centrifuge drawer 6800 may further comprise two or more wheels 6810 coupled to frame 6804.

The centrifuge typically receives power and communications capability through cables that connect the centrifuge module power source. Centrifuge drawer 6800 may include a feature for managing cables when the drawer is extended and retracted. In some embodiments, centrifuge drawer 6800 comprises a flexible cable container such as e-chain 6812 as shown in retracted position 6812(*a*) and extended position 6812(*b*) in FIG. 13. Although e-chain 6812 is shown in both retracted and extended positions for illustrative purposes, typically centrifuge drawer 6800 would have a single e-chain 6812 that would move between positions 6812(*a*) and 6812(*b*) as the drawer is operated. E-chain 6812 may contain cables such as power and communication cables. E-chain 6812 may be constructed from a flexible material such as a flexible plastic configured to extend and retract such that cables contained within e-chain 6812 do not interfere with the operation of centrifuge drawer 6800.

Figure 14A:
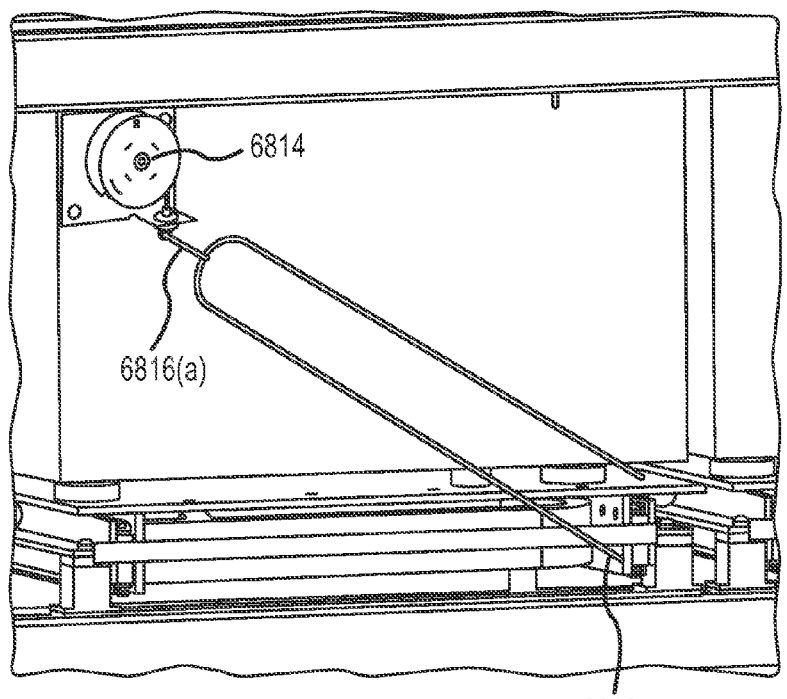
FIGS. 14(a)-(b) show an illustrative cable management device for a centrifuge drawer, according to a second embodiment.
Figure 14B:
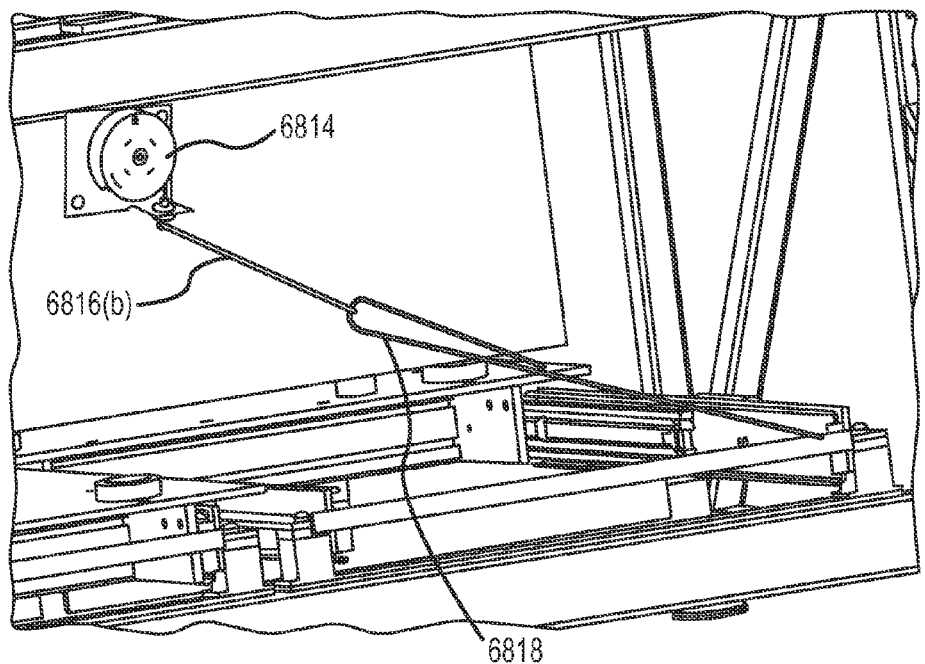

In another embodiment, a cable retractor 6814 can be used to manage cables, as shown in FIGS. 14(*a*)-14(*b*). Cable retractor 6814 may use a spring loaded cable retractor 6816 coupled to frame 6804 to keep one or more cables 6818 from interfering with the operation of centrifuge drawer 6800. Spring loaded cable retractor 6816 is shown in retracted position 6816(*a*) and extended position 6816(*b*). A spring in spring loaded cable retractor 6816 includes a spring 6816(*a*), 6816(*b*) coupled to a cable associated with the centrifuge. When the drawer is extended, the spring 6816(*a*), 6816(*b*) extends, allowing the cable to extend without coming into contact with the drawer. When the drawer is retracted, the spring compresses, pulling the cable away from frame 6804.

In some embodiments, centrifuge drawer 6800 includes a movement prevention measure. Movement of the drawer while the centrifuge is in operation could cause rotor imbalance and/or collision between the rotor bucket and containment can. Centrifuge drawer 6800 may include a permanent magnet with electric override to hold the centrifuge in place. To operate the drawer (e.g., to extend the drawer), the magnetic force of the permanent magnet is overpowered by application of an electric current to the electromagnet. For example, the electromagnet current may be activated with a polarization to counteract the magnetic field of the permanent magnet.

Figure 15:
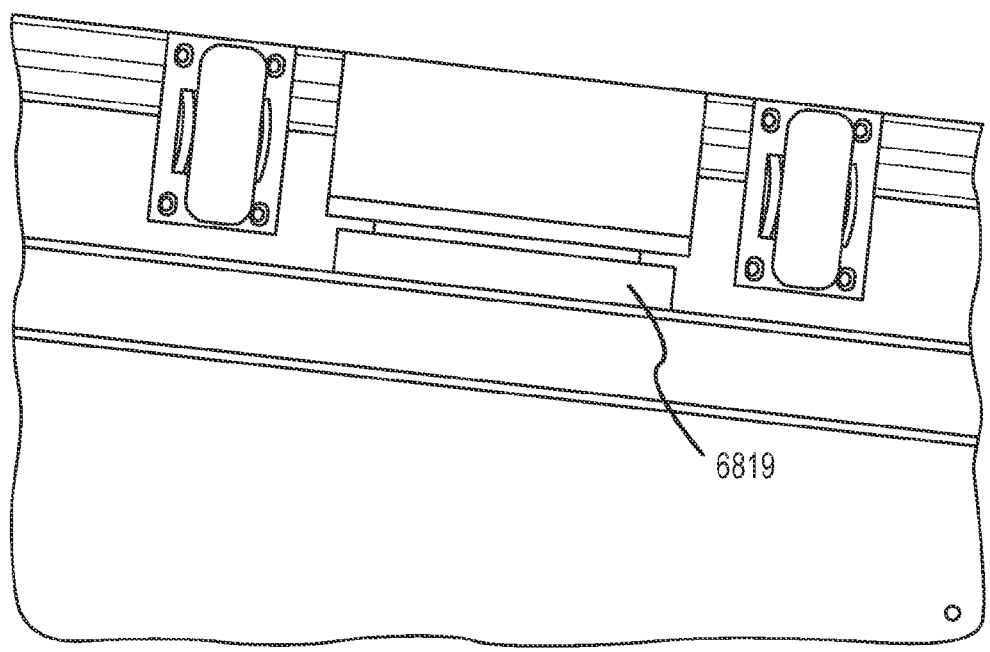
FIG. 15 shows an illustrative magnetic latch for a centrifuge drawer.

The centrifuge drawer 6800 may include a permanent magnet with electromagnet override latch 6819 as shown in FIG. 15. The permanent magnet latch may be installed between wheels 6810 of centrifuge drawer 6800. The permanent magnet may hold the drawer in a fully retracted state when the drawer is retracted. For example, the electromagnet current may be activated with a polarization to reinforce the magnetic field of the permanent magnet. The force of the permanent magnet may be sufficient to hold centrifuge drawer in place while the centrifuge is not running. In some embodiments, the electromagnet 6819 is engaged to hold the drawer in a fully retracted state when the centrifuge is running.

Figure 16A:
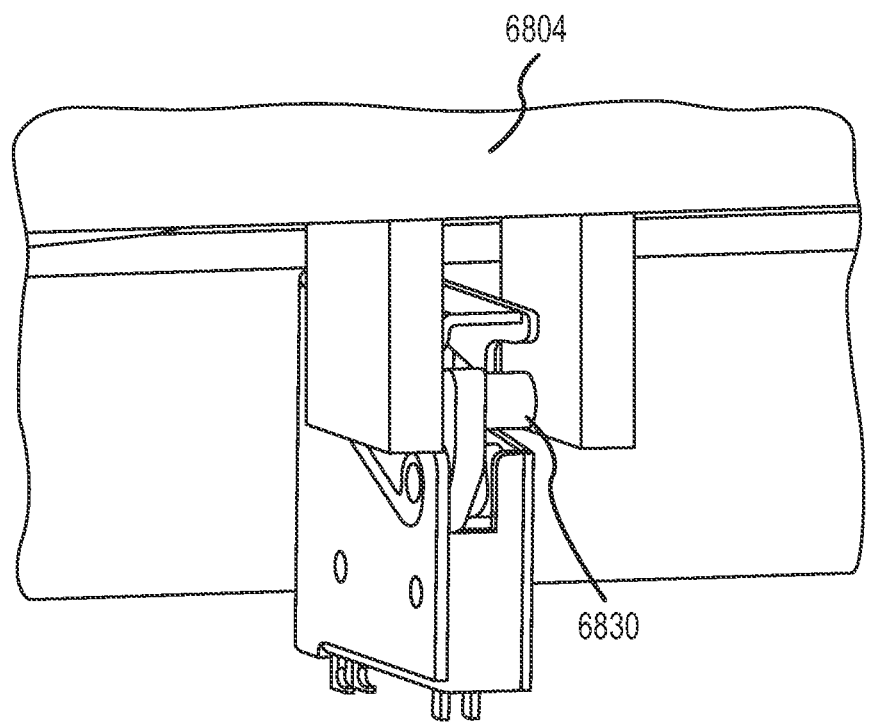
FIGS. 16(a)-(c) show an illustrative mechanical latch for a centrifuge drawer.
Figure 16B:
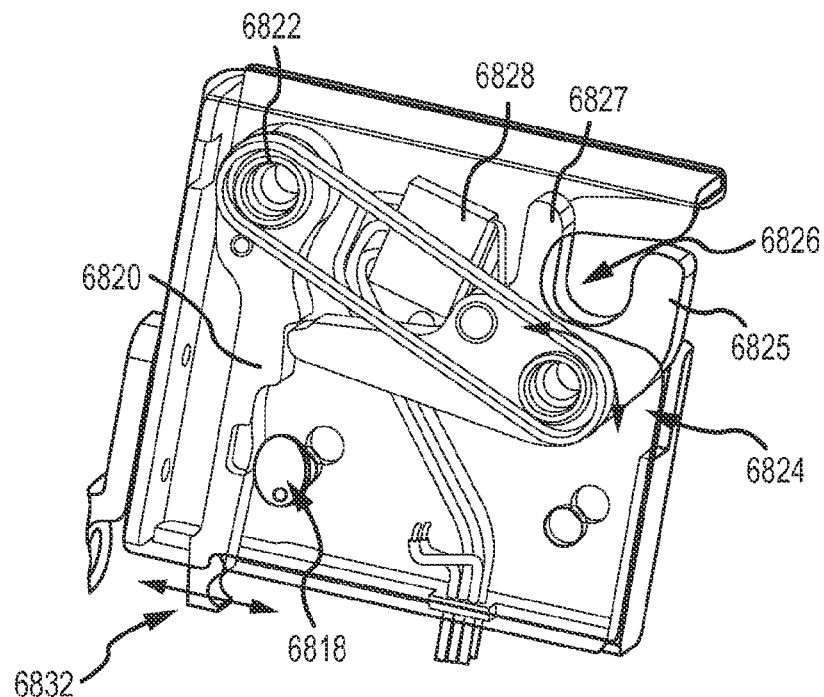
Figure 16C:
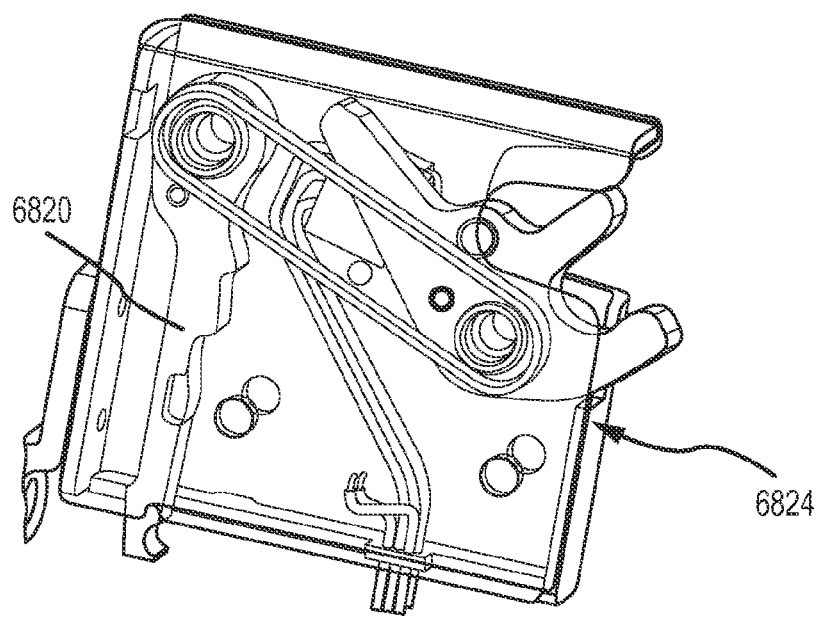
Figure 17:
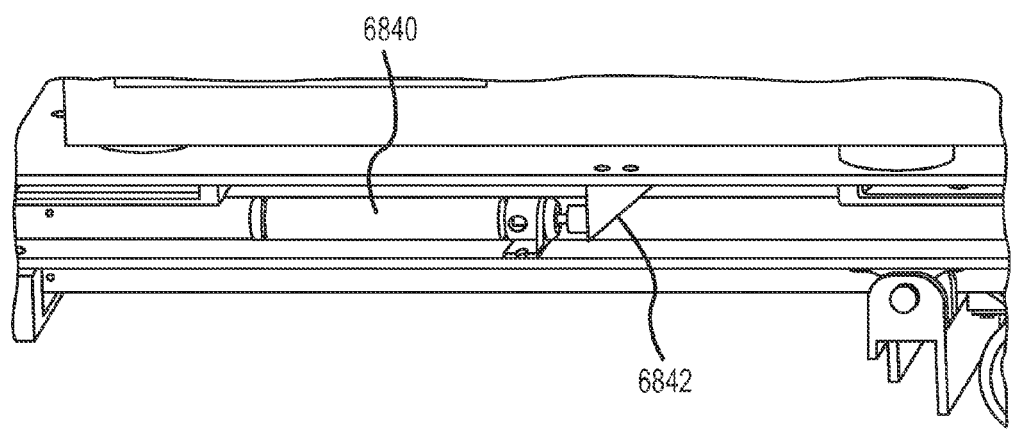
FIG. 17 shows an illustrative compression damper for a centrifuge drawer.

Centrifuge drawer 6800 may comprise an electric rotary mechanical latch. FIG. 16(*a*) shows a perspective view of the mechanical latch and FIG. 16(*b*) shows a cross-sectional view of the mechanical latch. To extend the drawer, an electrical signal is sent from a controller to the latch and, in response, an electric motor rotates cam 6818. The controller may be a latch controller, a centrifuge drawer controller, a centrifuge controller, or another controller. The rotation of cam 6818 causes latch element 6820 to rotate about pivot 6822. Latch element 6820 may be a bar shaped to interface with latch element 6824. Latch element 6820 may also have a cable override element 6832 that will allow the drawer to be extended when power is lost in the event of a power failure. Latch element 6824 may have a first tine 6825 and a second tine 6827. The tines 6825, 6827 can restrain the movement of a striker bolt 6830 when the striker bolt is within opening 6826. Striker bolt 6830 is attached to the drawer frame 6804. The rotation of latch element 6820 around pivot 6822 causes latch element 6824 to be released. A spring (not shown), which may be a torsion spring, such as a weak torsion spring, can cause latch element 6825 to rotate clockwise when latch element 6824 is not restrained by latch element 6820. The operation of drawer 6800 to retract the drawer can also cause latch element 6824 to rotate clockwise. When latch element 6824 has rotated such that opening 6826 is no longer blocked by tine 6825 of the latch element, the striker bolt 6830 is no longer restrained and the drawer can be extended. FIG. 16(*c*) shows the configuration of latch elements 6820, 6824 when the latch is in an open position such that striker bolt 6830 is no longer restrained.

Latch sensor 6828 may be capable of detecting the position of the drawer. When the drawer is in a retracted position, latch sensor 6828 can send a signal to rotate cam 6818 such that 6820 is returned to the position shown in FIG. 16(*b*). Counterclockwise rotation of 6825 (e.g., by urging striker bolt 6830 against tine 6827 to return latch element 6824 to the position shown in FIG. 16(*b*). In this way, the drawer 6800 can be mechanically locked once it is refracted.

In some embodiments, centrifuge drawer 6800 comprises a damping mechanism to mitigate vibration of the frame 6804 when the drawer is being retracted to allow the centrifuge module to continue processing samples. A damping mechanism such as the compression damper 6840 shown in FIG. 17 can be used to couple frame 6804 to platform 6802 via the damper contractor 6842 such that a force exerted to retract the drawer is speed controlled compression damper 6840. The compression damper may be a gas or fluid damper. In some embodiments, the gas damper allows the centrifuge to be retracted freely until a state requiring control is reached.

Figure 18:
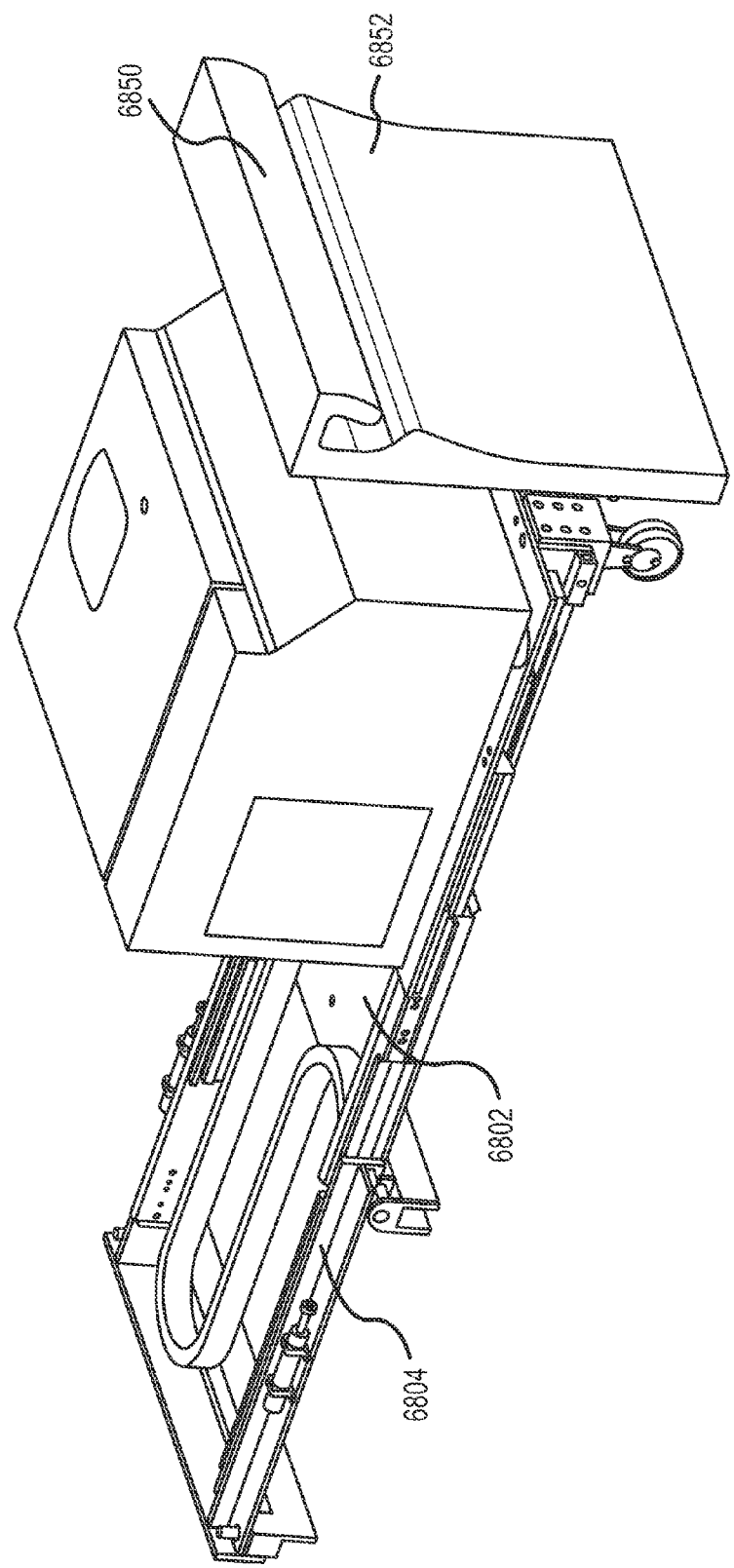
FIG. 18 shows an illustrative cover for a centrifuge drawer.

FIG. 18 shows a cover for a centrifuge drawer. Cover 6850 can be removed from the centrifuge drawer 6800 to allow access to drawer frame 6804 for loading the centrifuge onto the platform 6802. Cover 6850 may include a handle 6852 to provide a user with a gripping point to extend the centrifuge.

Figure 19:
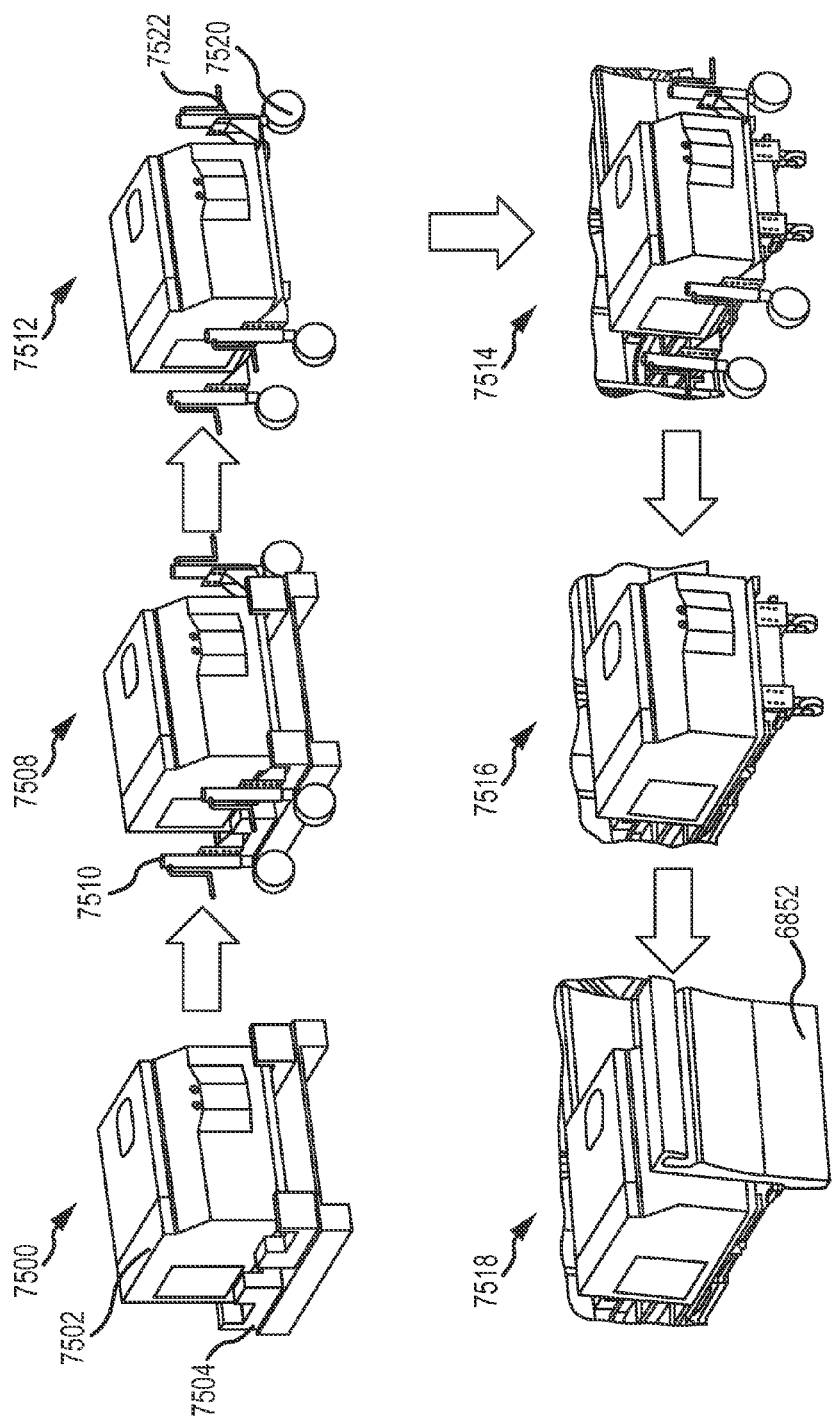
FIG. 19 shows an illustrative workflow for loading a centrifuge onto a centrifuge drawer.

FIG. 19 illustrates a workflow for loading a centrifuge onto drawer 6800. At 7500, centrifuge 7502 is in crate 7504. For example, the centrifuge may have been recently shipped to the laboratory. At 7508, a loading tool 7510 having may be applied to the centrifuge 7502. Loading tool 7510 may have a plurality of wheels 7520 and a plurality of jacks 7522. At 7512, the centrifuge is jacked up by extending the jacks of loading tool 7510. At this point, crate 7504 can be removed. At 7514, centrifuge 7502 can be rolled over drawer 6800 using loading tool 7510. The jacks can be retracted such that the centrifuge 7502 is supported by centrifuge drawer 6800. At 7516, loading tool 7510 is removed. At 7518, cover 6852 can be attached to drawer 6800.

Centrifuge Adapter Gripper

A robotic arm may be capable of picking up and transporting a centrifuge adapter. For example, centrifuge adapters that are loaded with sample tubes ready to be centrifuged may be transported from the distribution area 204 to the centrifuge module 206 via a shuttle 224. The centrifuge adapters are loaded into the centrifuge, after which the samples can be centrifuged.

Figure 20B:
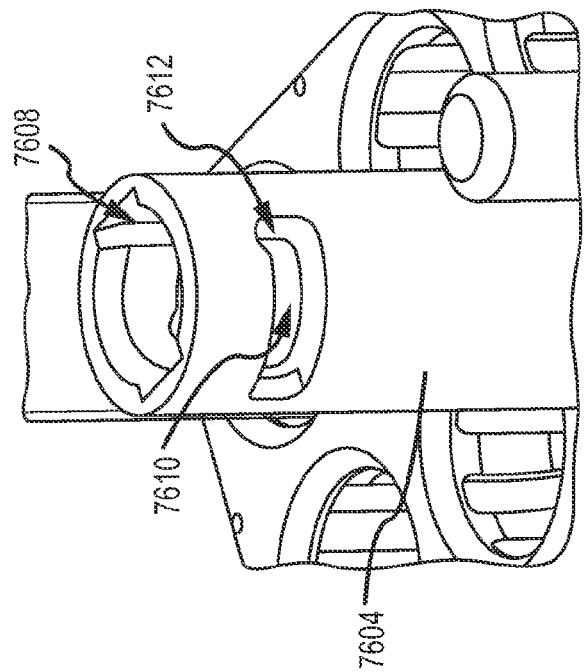
FIGS. 20(a)-(b) show an illustrative centrifuge adapter gripper, according to a first embodiment.
Figure 20A:
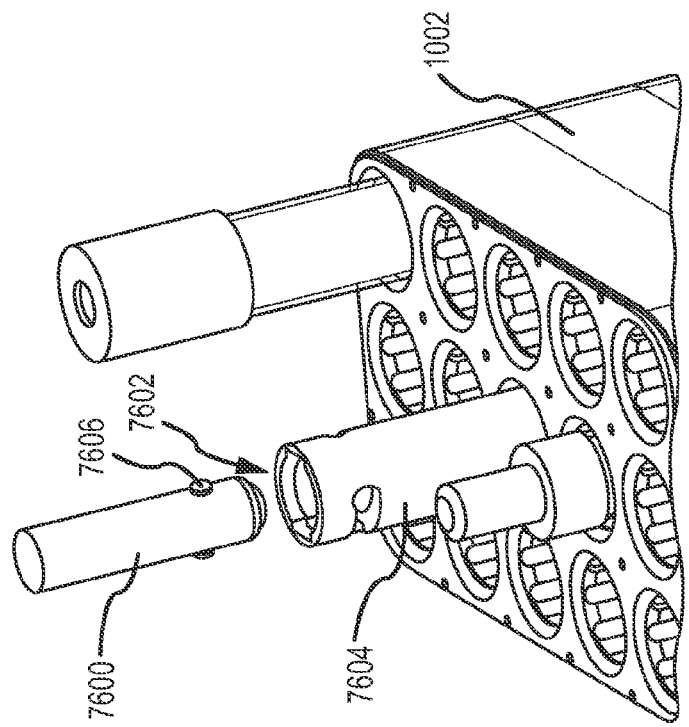

FIG. 20(*a*) shows an illustrative gripper element of a centrifuge adapter gripper. Centrifuge adapter gripper 227 (not shown) may comprise a gripper element 7600 coupled to a robotic arm. Gripper element 7600 may be a bolt. The bolt 7600 may be rounded at tip 7602 to allow the bolt 7600 to be inserted into a dedicated hooking element in centrifuge adapter tubular holder 7604. The bolt 7600 may comprise lateral pins 7606 coupled to opposing sides of bolt 7600. When bolt 7600 is rotated to a locked position within tubular holder 7604, the gripper can lift up centrifuge adapter 1002.

FIG. 20(*b*) shows tubular holder 7604, according to a first embodiment. Tubular holder 7604 may comprise vertical grooves 7608 configured to receive pins 7606 of bolt 7600. Tubular holder 7604 may also comprise horizontal grooves 7610. Each horizontal groove 7610 may connect to a vertical groove 7608. In some embodiments, horizontal groves 7610 may be slots in tubular holder 7604. When bolt 7600 is inserted into tubular holder 7604, gripper pins 7606 may be guided downward by vertical grooves 7608. Gripper 227 may rotate bolt 7600 (e.g., by 90 degrees) such that the pins 7606 follow the horizontal grooves 7610 in tubular holder 7604 until pins 7606 reach the gripping position indicated by notches 7612. In this manner, the gripper can lift and transport centrifuge adapter 1002. To release bolt 7600 from centrifuge adapter tubular holder 7604, the bolt is rotated in the opposite direction.

Figure 21B:
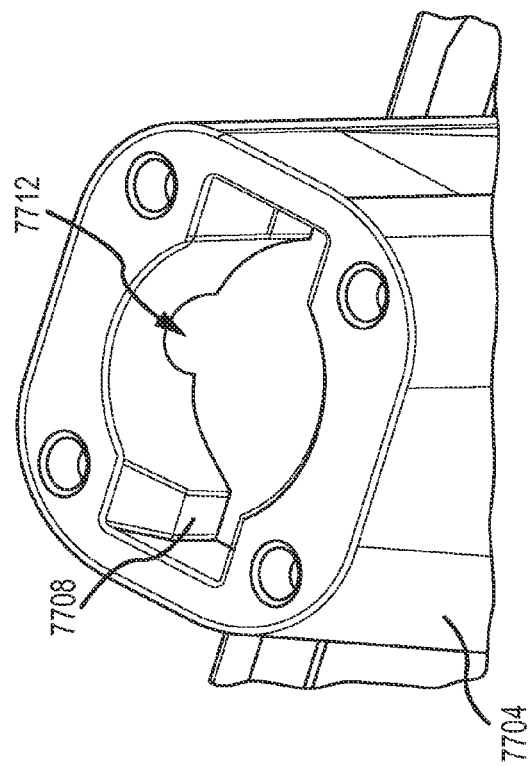
FIGS. 21(a)-(b) show an illustrative centrifuge adapter gripper, according to a second embodiment.
Figure 21A:
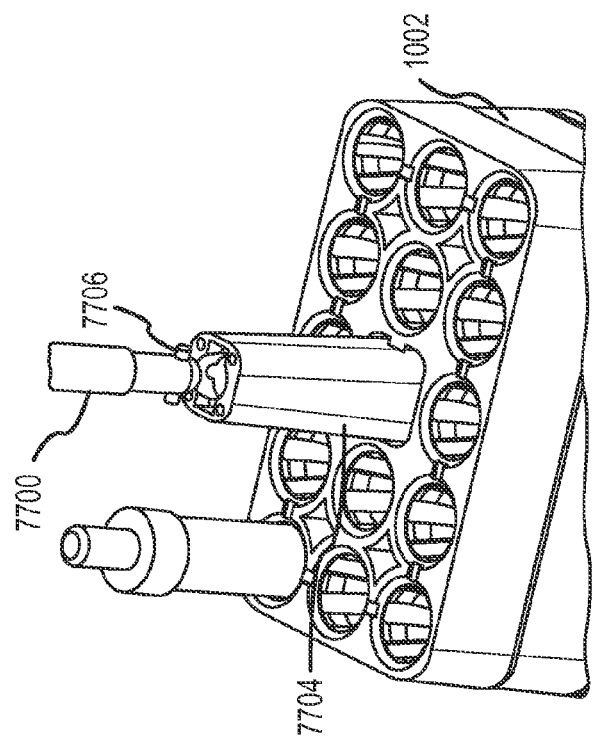

FIGS. 21(*a*)-21(*b*) show tubular holder 7704, according to a second embodiment. Tubular holder 7704 may have a keyhole opening 7712 configured to match the cross-sectional profile of bolt 7700 with pins 7706. When bolt 7700 is inserted into tubular holder 7704, gripper pins 7606 fit through keyhole opening 7712 and are lowered below a shelf 7708. When the pins 7706 are below shelf 7708, gripper 227 may rotate bolt 7700 (e.g., by 90 degrees) such that the pins 7706 are seated in notch 7712. In this manner, the gripper can lift and transport centrifuge adapter 1002. To release bolt 7700 from centrifuge adapter tubular holder 7704, the bolt is rotated in the opposite direction.

Various measures may be implemented to prevent the centrifuge adapter from swinging during x- and y-axis movement of centrifuge adapter gripper 227. For example, gripper 227 may be operated at the extent of its z-axis range such that the top of the adapter is pressed against the underside of the housing of gripper 227. In this manner, any motion of centrifuge adapter 1002 with respect to gripper may be damped. In some embodiments, one or more springs may be used to prevent vibrations from the gripper housing from causing swinging of the centrifuge adapter.

In some embodiments, a robotic arm may be a combined gripper capable of gripping sample tubes as well as adapters 1002 used in the centrifuge module 206. One or more centrifuge area grippers may perform several functions, including picking up sample tubes at an input area 202, transporting sample tubes to a loading position 1004 for an empty centrifuge bucket, placing sample tubes in a free position of the centrifuge adapter, choosing a completely (or incompletely) filled centrifuge adapter, transporting the centrifuge adapter to an available centrifuge, placing the centrifuge adapter in a free position of the centrifuge rotor, choosing a centrifuged adapter, transporting a centrifuged adapter to an unloading position for a centrifuged adapter, picking up centrifuged sample tubes in the centrifuged adapter, etc.

In another embodiment, a single sample tube gripper can be applied to a telescopic robotic arm. The sample tube gripper unit may be moved down into the centrifuge body using the telescopic robotic arm. The sample tube gripper robot may then grip the centrifuge buckets with its standard gripper unit.

In another embodiment, a centrifuge bucket gripper unit can be applied to the telescopic robotic arm in addition to a standard sample tube gripper.

Centrifuge Adapter Lift-Up Prevention

A sticky label or stuck specimen tube may cause a centrifuge adapter 1002 to become airborne when centrifuge tube gripper 226 removes a sample tube from an adapter. Various lift-up prevention devices to prevent adapters 1002 from becoming airborne are described below. Typically, a lift-up prevention device is activated only when sample tubes are being loaded into and unloaded from adapters, allowing the adapters to move freely when adapters are being moved.

FIGS. 22(*a*)-(*c*) show an illustrative hook lift-up prevention device. In some embodiments, an adapter has a mechanical locking feature. For example, adapter 1002, shown in FIG. 22(*a*), may comprise an opening 7902. Shuttle 224, shown in FIG. 22(*b*), may have hook 7906 configured to be inserted into opening 7902. The hook is configured to be inserted into opening 7902 and to hold adapter 1002 to shuttle 224 when hook 7906 is inserted into opening 7902 of adapter 1002.

When the shuttle is moved to a position at which tubes can be unloaded from an adapter 1002, hook 7906 is inserted through opening 7902 and, subsequently, adapter 1002 is shifted such that hook 7906 overhangs a ledge in opening 7902 to prevent adapter 1002 from lifting off of shuttle 224, as shown in FIG. 22(*c*). When adapter 1002 is shifted into the adapter swapping position, the hook mechanism may be disengaged.

FIG. 23 shows an illustrative magnetic lift-up prevention device. In some embodiments, a ferromagnetic object, such as metal object 8000 (e.g., a steel bar) may be coupled to adapter 1002. For example, steel bar 8000 may be coupled to underside of adapter 1002 that rests on shuttle 224. When the shuttle is in an unloading position, stationary electromagnet (not shown) under steel bar 8000 may be powered in order to create a magnetic field to attract steel bar 8000 to the stationary electromagnet. The electromagnet may receive power from a power supply coupled to a controller in response to a signal sent to the power supply from the controller. The controller may be a centrifuge adapter shuttle controller or another controller. In this manner, adapter 1002 can be held in place during unloading. When unloading of adapter 1002 is complete, power to the stationary electromagnet can be discontinued to allow adapter 1002 to be moved. The magnetic lift-up prevention approach advantageously requires no mechanical parts and can be quickly activated and de-activated.

Computer Apparatus

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, centrifuge controller, balance controller, etc.

Figure 24:
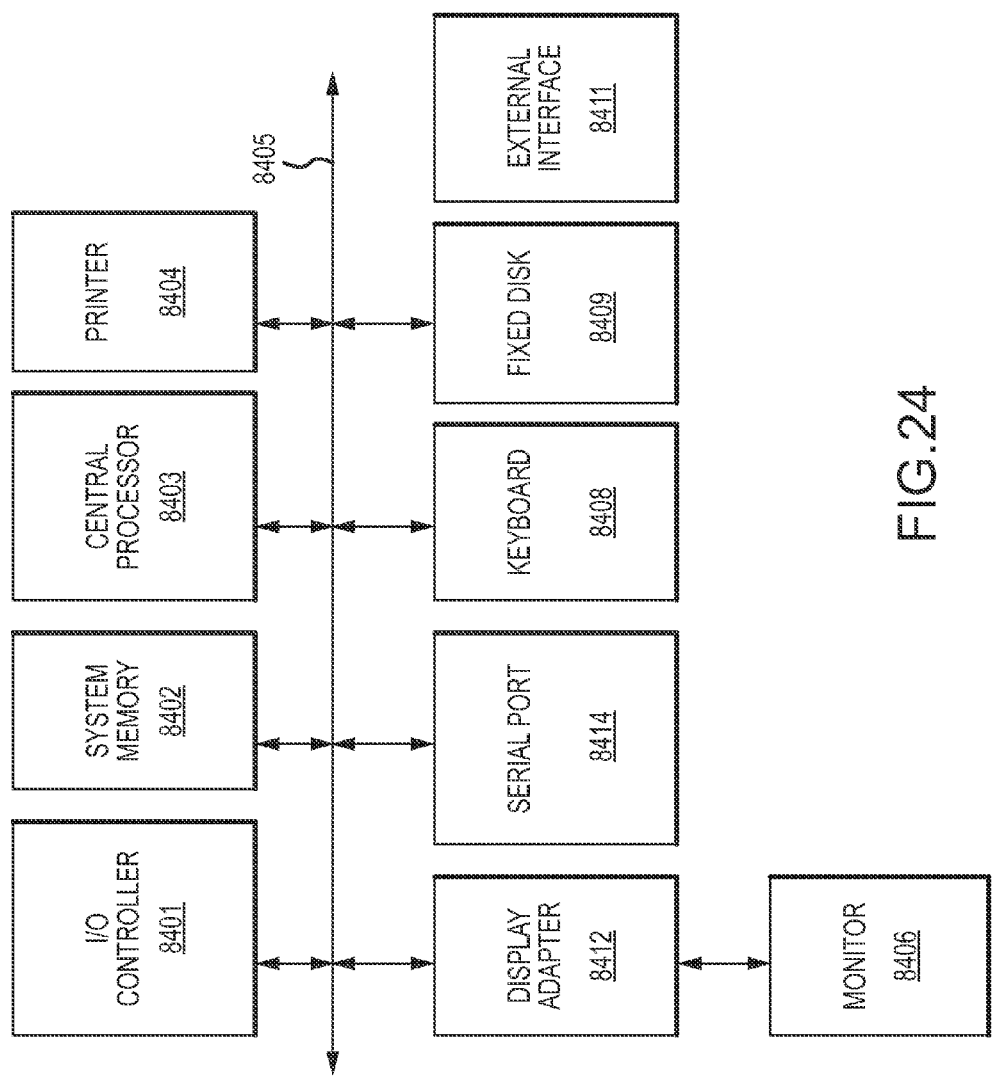
FIG. 24 depicts a block diagram of an exemplary computer apparatus.

Examples of such subsystems or components are shown in FIG. 24. The subsystems shown in FIG. 84 are interconnected via a system bus 8405. Additional subsystems such as a printer 8404, keyboard 8408, fixed disk 8409 (or other memory comprising computer readable media), monitor 8406, which is coupled to display adapter 8412, and others are shown. Peripherals and input/output (I/O) devices, which couple to I/O controller 8401 (which can be a processor or other suitable controller), can be connected to the computer system by any number of means known in the art, such as serial port 8414. For example, serial port 8414 or external interface 8411 can be used to connect the computer apparatus to a wide area network such as the Internet, a mouse input device, or a scanner. The interconnection via system bus allows the central processor 8403 to communicate with each subsystem and to control the execution of instructions from system memory 8402 or the fixed disk 8409, as well as the exchange of information between subsystems. The system memory 8402 and/or the fixed disk 8409 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology. For example, any features of any two or more specific embodiments as described above, can be combined in any suitable manner without departing from the spirit and scope of the invention.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method for processing medical samples in a laboratory system comprising:
   transporting by an input module gripper a plurality of specimen containers from an input module to a distribution area module;
   detecting test information about the specimen containers with a first camera coupled to the input module gripper and optically measuring liquid levels within the specimen containers during the transport to the distribution area module via transmission measurement with an emitter unit and a receiver unit, wherein the emitter unit and the receiver unit are coupled to the input module gripper;
   loading, by a distribution area gripper in the distribution area module, the plurality of specimen containers into a centrifuge adapter which is placed on an adapter shuttle;
   transporting, by the adapter shuttle, the centrifuge adapter from the distribution area module to a centrifuge module, which comprises a centrifuge;
   transporting, by a centrifuge adapter gripper, the centrifuge adapter into the centrifuge;
   centrifuging, by the centrifuge, the centrifuge adapter; and
   transporting, by the centrifuge adapter gripper, the centrifuge adapter from the centrifuge to the adapter shuttle; and
   unloading, by a centrifuge tube gripper in the centrifuge module, the plurality of specimen containers from the centrifuge adapter.

2. The method of claim 1,
   wherein a weight of one or more specimen containers of the plurality of specimen containers is determined prior to loading, by the distribution area gripper, the plurality of specimen containers into the centrifuge adapter.

3. The method of claim 2,
   wherein the weight of the one or more specimen containers is determined by the input module gripper configured to transport specimen containers to the distribution area module from which the distribution area gripper grips the plurality of specimen containers, and
   wherein the plurality of specimen containers are loaded into the centrifuge adapter in a sequential order based on the weight of the plurality of specimen containers.

4. The method of claim 1,
   wherein the centrifuge tube gripper is used to determine a quantity of liquid in the specimen container, wherein the liquid comprises one or more liquids.

5. The method of claim 1,
   wherein the test information associated with the specimen containers is accessed by the system in order to create, by a scheduler, a specimen container schedule to plan an analysis process for the specimen containers and
   wherein the distribution area gripper selects a specimen container that is, according to the schedule, next to be transferred to the centrifuge module from the distribution area module.

6. The method of claim 5, wherein
   the centrifuge adapter gripper is used to swap centrifuge adapters into and out of the centrifuge and wherein the centrifuge adapters, loaded with specimen containers, arriving at the centrifuge module from the distribution area module via the adapter shuttle, are loaded into an available centrifuge bucket.

7. The method of claim 1 wherein
   the centrifuge tube gripper is used to transport the specimen container to a carrier on a conveyance system of the laboratory system.

8. The method of claim 7, wherein
   as the specimen container is moved from the centrifuge adapter to the carrier, a liquid level detection is performed with the centrifuge tube gripper to ensure that tests required for the specimen comprised in the specimen container can be completed, and wherein,
   if it is detected that insufficient sample material is present in the specimen container, the specimen container is processed according to procedures established for insufficient sample material conditions.

9. The method of claim 1, wherein the centrifuge is mounted on a moveable drawer, wherein the moveable drawer is moveable between an extended position and a retracted position, wherein the centrifuge is powered and controlled via at least one cable connecting to the centrifuge, and wherein a cable management feature controls the cable during the movement of the moveable drawer between the extended and retracted positions.

10. The method of claim 9, wherein the cable management feature comprises an e-chain.

11. The method of claim 1, wherein the first camera is positioned to detect test information about the specimen containers in a rack.

12. The method of claim 11, wherein the input module gripper comprises a plurality of gripper fingers manipulable to grip the specimen containers, and wherein the receiver unit is laterally offset from the gripper fingers.

* * * * *